(12) United States Patent
Pomper et al.

(10) Patent No.: US 11,078,166 B2
(45) Date of Patent: Aug. 3, 2021

(54) TRIAZOLE CONJUGATED UREAS, THIOUREAS, CARBAMATES, AND REVERSED CARBAMATES FOR PSMA-TARGETED IMAGING AGENTS AND USES THEREOF

(71) Applicant: THE JOHNS HOPKINS UNIVERSITY, Baltimore, MD (US)

(72) Inventors: Martin G. Pomper, Baltimore, MD (US); Ying Chen, Lutherville-Timonium, MD (US); Xing Yang, Baltimore, MD (US); Ronnie C. Mease, Fairfax, VA (US); Sangeeta Ray, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 118 days.

(21) Appl. No.: 15/752,340

(22) PCT Filed: Aug. 15, 2016

(86) PCT No.: PCT/US2016/046981
§ 371 (c)(1),
(2) Date: Feb. 13, 2018

(87) PCT Pub. No.: WO2017/027870
PCT Pub. Date: Feb. 16, 2017

(65) Prior Publication Data
US 2019/0225589 A1 Jul. 25, 2019

Related U.S. Application Data

(60) Provisional application No. 62/204,697, filed on Aug. 13, 2015.

(51) Int. Cl.
| *C07D 249/04* | (2006.01) |
| *A61K 51/04* | (2006.01) |
| *C07B 59/00* | (2006.01) |

(52) U.S. Cl.
CPC ........ *C07D 249/04* (2013.01); *A61K 51/0402* (2013.01); *A61K 51/0453* (2013.01); *C07B 59/002* (2013.01); *A61K 2123/00* (2013.01); *C07B 2200/05* (2013.01)

(58) Field of Classification Search
CPC . C07D 249/04; C07B 2200/05; C07B 59/002; A61K 2123/00
See application file for complete search history.

(56) References Cited

FOREIGN PATENT DOCUMENTS

| WO | 2013028664 A1 | 2/2013 |
| WO | 2014143736 A1 | 9/2014 |

OTHER PUBLICATIONS

International Search Report with Written Opinion for Application No. PCT/US2016/046981 dated Nov. 11, 2016 (19 pages).
International Preliminary Report on Patentability with Written Opinion for Application No. PCT/US2016/046981 dated Feb. 22, 2018 (14 pages).
Ying Chen, et al. ,"Fluoroethyl Triazole Substituted PSMA Inhibitor Exhibiting Rapid Normal Organ Clearance", Bioconjugate Chemistry, 2016, vol. 27, pp. 1655-1662.
Li Bryan et al, "Aqueous Phosphoric Acid as a Mild Reagent for Deprotection of tert-Butyl Carbamates, Esters, and Ethers", Journal of Organic Chemistry, 2006, vol. 71, pp. 9045-9050.
Jan Marik, "Click for PET: rapid preparation of [18F]fluoropeptides using CuI catalyzed 1,3-dipolar cycloaddition", Tetrahedron Letters, 2006, vol. 47, pp. 6681-6684.

*Primary Examiner* — James W Rogers
(74) *Attorney, Agent, or Firm* — Casimir Jones, S.C.; Jeffrey W. Childers

(57) ABSTRACT

Triazole conjugated urea-based and thiourea-based scaffolds that have high binding affinity to PSMA are disclosed. These scaffolds can be radiolabeled and used to image cells and tumors that express PSMA. Methods of synthesizing radiofluorinated triazole conjugated urea-based and thiourea-based scaffolds also are disclosed.

1 Claim, 15 Drawing Sheets
(4 of 15 Drawing Sheet(s) Filed in Color)

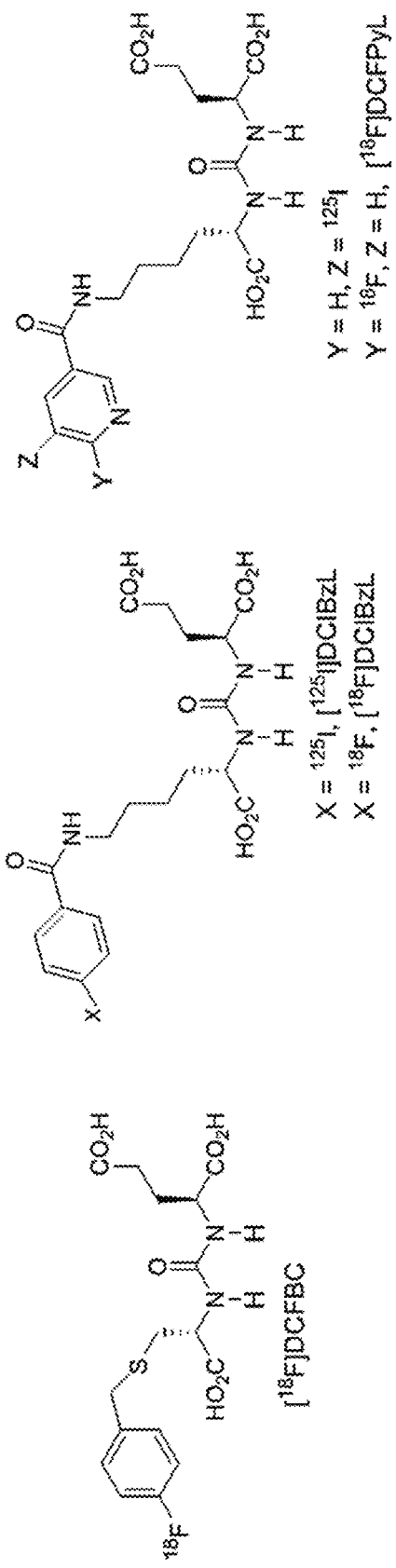
Fig. 1B *(prior art)*

AC-A1

YC-A2

YC-A3

YC-A4

YC-A5

YC-A6

YC-A7

TC-A8 n, m, p, q, r and s could be number between 0 to 10
X = O or S

TRIAZOLE CONJUGATED UREAS, THIOUREAS, CARBAMATES, AND REVERSED CARBAMATES FOR PSMA-TARGETED IMAGING AGENTS AND USES THEREOF

CROSS-REFERENCE TO RELATED APPLICATIONS

This application is a 35 U.S.C. § 371 National Stage Entry of International Application No. PCT/US2016/046981 having an international filing date of Aug. 15, 2016, which claims the benefit of U.S. Provisional Application No. 62/204,697, filed Aug. 13, 2015, the contents of which are incorporated herein by reference in their entirety.

BACKGROUND

The prostate-specific membrane antigen (PSMA) is a type II integral membrane protein expressed on the surface of prostate tumors, particularly in castrate-resistant, advanced and metastatic disease (Huang et al., *Prostate* 2004; Schuelke et al., *Proc. Natl. Acad. Sci. U.S.A.* 2003). PSMA also is expressed in neovascular endothelium of most solid tumors, such as lung, colon, pancreatic, renal carcinoma and skin melanoma, but not in normal vasculature (Liu et al., *Cancer research* 1997; Chang et al., *Cancer research* 1999), which makes it an excellent target for imaging and targeted therapy of these cancers.

A series of PSMA-targeted imaging agents for positron emission tomography (PET) imaging of prostate cancer has been previously developed (Kiess et al., *Q. J. Nucl. Med. Mol. Imaging* 592015), and several $^{68}$Ga- and $^{18}$F-radiolabeled imaging agents have been evaluated in clinical studies (Cho et al., *J. Nucl. Med.* 2012; Afshar-Oromieh et al., J. Nucl. Med. Mol. Imaging 2012; Afshar-Oromieh et al., *J. Nucl. Med. Mol. Imaging* 2013; Afshar-Oromieh et al., *J. Nucl. Med. Mol. Imaging* 2014; Eiber et al., *J. Nucl. Med.* 2015; Eiber et al., *Abdominal Imaging* 2015; Rowe et al., *J. Nucl. Med.* 2015; Dietlein et al., *Molecular Imaging and Biology* 2015; Szabo et al., *Molecular Imaging and Biology* 2015). It has been chosen to focus on $^{18}$F-labeled compounds in part because the infrastructure in the U.S.A. is currently more amenable to such agents relative to those labeled with $^{68}$Ga. A series of $^{18}$F-labeled, PSMA-targeted imaging agents has been previously developed (FIG. 1), including N—[N—[(S)-1,3-dicarboxypropyl]-carbamoyl]-4-[$^{18}$F]fluorobenzyl-L-cysteine ([$^{18}$F]DCFBC), 2-[3-[1-carboxy-5-(4-[18F]fluoro-benzoylamino)-pentyl]-ureido]-pentanedioic acid ([$^{18}$F]DCFBzL), and 2-(3-{1-carboxy-5-[(6-[$^{18}$F]fluoropyridine-3-carbonyl)-amino]-pentyl}-ureido)-pentanedioic acid ([$^{18}$F]DCFPyL). Mease et al., *Clin. Cancer Res.* 2008; Chen et al., *J. Med. Chem.* 2008; and Chen et al., *Clin. Cancer Res.* 2011. Phase I trials of [$^{18}$F]DCFBC and [$^{18}$F]DCFPyL to image metastatic prostate cancer have recently been completed, and both have shown promising results (Cho et al., *J. Nucl. Med.* 2012; Szabo et al., *Molecular Imaging and Biology* 2015). One drawback of [$^{18}$F]DCFBC was that it showed moderate, persistent blood-pool radioactivity (Cho et al., *J. Nucl. Med.* 2012), which could be a limitation for the detection of lymph node metastases adjacent to major vessels. Clinical imaging studies of [$^{18}$F]DCFPyL showed lower blood pool activity, providing clearer images than [$^{18}$F]DCFBC; however, considerable kidney and salivary gland uptake of this tracer was observed and may result in dose limiting toxicities in these organs (Szabo et al., *Molecular Imaging and Biology* 2015). In spite of the multistep synthetic procedure required, the radiosynthesis of both agents has been automated to produce several clinical doses per synthesis for on-site use. However, further improvements in yield may be needed for regional distribution on a model similar to that for [$^{18}$F]fluorodeoxyglucose (FDG). Therefore, a need still exists for an $^{18}$F-labeled PSMA inhibitor that could be prepared quickly, in high yield, and that could localize to PSMA-positive lesions but clear rapidly from normal organs.

SUMMARY

In some aspects, the presently disclosed subject matter provides a compound of formula (I):

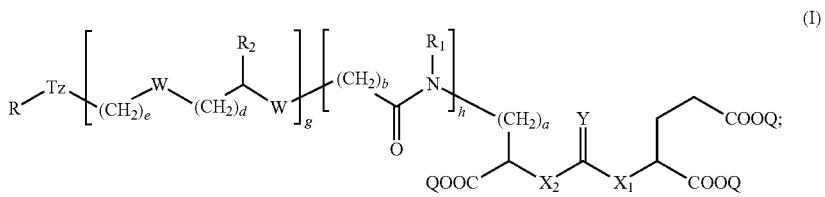

wherein: Z is tetrazole or $CO_2Q$; Q is H or a protecting group; Y is O or S; $X_1$ and $X_2$ are each independently selected from the group consisting of O and NH;

a, b, d, and e are each an integer independently selected from the group consisting of 0, 1, 2, 3, 4, 5, 6, 7, 8, 9, and 10; g and h are each independently 0 or 1; each $R_1$ is independently H or $C_1$-$C_4$ alkyl; each $R_2$ is independently H or COOH; each W is independently selected from the group consisting of —C(=O)—NR$_2$—, —NR$_2$—C(=O)—, —NR$_2$—C(=O)—NR$_2$—, —NR$_2$—C(=S)—NR$_2$—, —NR$_2$—C(=O)—O—, —O—C(=O)—NR$_2$—, —O—C(=O)—, or —C(=O)—O—; Tz is a triazole selected from the group consisting of:

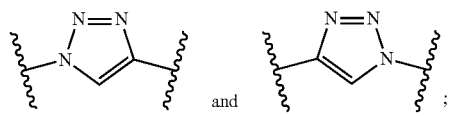 [SMILES: *c1cn(*)nn1 ; *c1cn(*)nn1]

and R is selected from the group consisting of substituted and unsubstituted alkyl, substituted and unsubstituted aryl, substituted and unsubstituted alkoxyl, each of which can comprise a radioactive isotope suitable for imaging or a halogen; and stereoisomers and pharmaceutically acceptable salts thereof.

In other aspects, the presently disclosed subject matter provides a method for imaging one or more prostate-specific membrane antigen (PSMA)-expressing tumors or cells, the method comprising contacting the one or more tumors or cells with an effective amount of a compound of formula (I) and making an image, wherein the compound of formula (I) further comprises a radioactive isotope suitable for imaging.

In other aspects, the presently disclosed subject matter provides a one-pot method of synthesizing a radiofluorinated compound of formula (I), the method comprising: (i) radiofluorinating a compound selected from the group consisting of

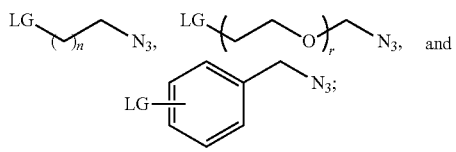

wherein LG is a leaving group; with [$^{18}$F]fluoride ion to form a radiofluorinated compound selected from the group consisting of

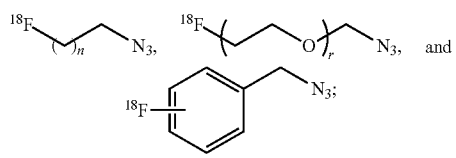

(ii) contacting the radiofluorinated compound (i) with copper (II) sulfate, sodium ascorbate, and a compound of formula (II):

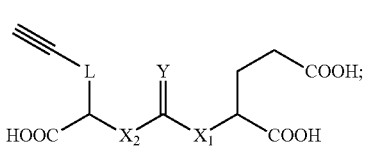

wherein L is

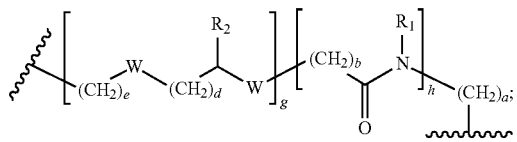

wherein a, b, d, e, g, $R_1$, W, and $R_2$ are defined hereinabove; Y is O or S; $X_1$ and $X_2$ are each independently selected from the group consisting of O and NH; to form a radiofluorinated compound of formula (I) in a reaction mixture; and (iii) purifying the radiofluorinated compound of formula (I) from the reaction mixture of step (ii) to provide a radiofluorinated compound of formula (I).

In other aspects, the presently disclosed subject matter provides a method of synthesizing radiofluorinated compound of formula (I); the method comprising:

(i) synthetizing a radiolabeled compound of formula (III') by reacting a compound of formula (II') with [$^{18}$F]fluoride ion;

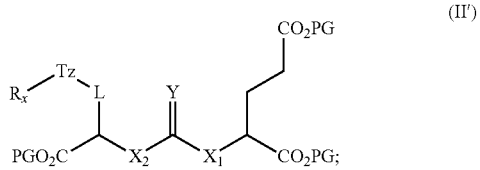

wherein $R_x$ is selected from the group consisting of:

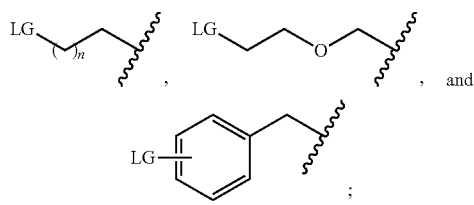

wherein each PG is a protecting group of an ester moiety that is removable by treatment with phosphoric acid, and LG is a leaving group;

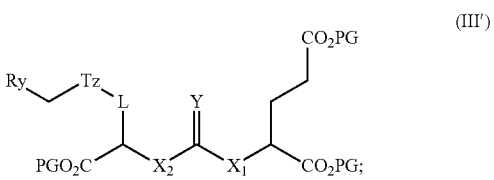

wherein Ry is selected from the group consisting of:

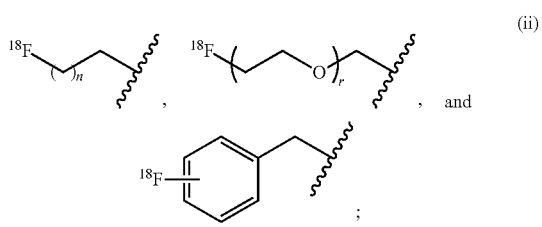

cleaving the protecting groups (PG) of the compound of formula (III') to obtain form a radiofluorinated compound of formula (I) in a reaction mixture; and (iii) purifying the radiofluorinated compound of formula (I) from the reaction mixture of step (ii) to provide a radiofluorinated compound of formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
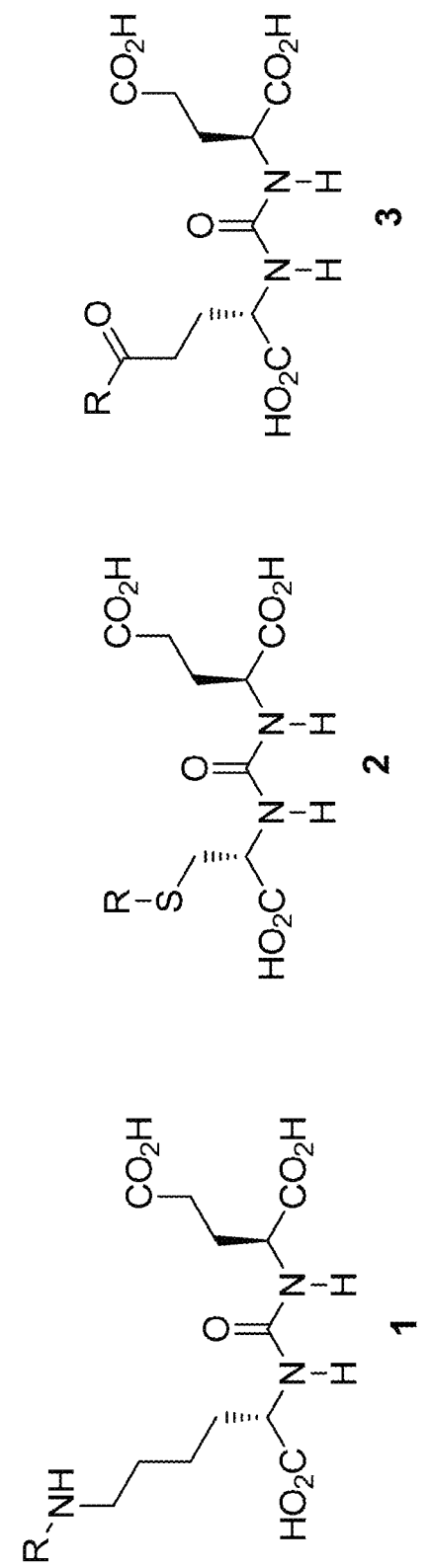
Figure 2:
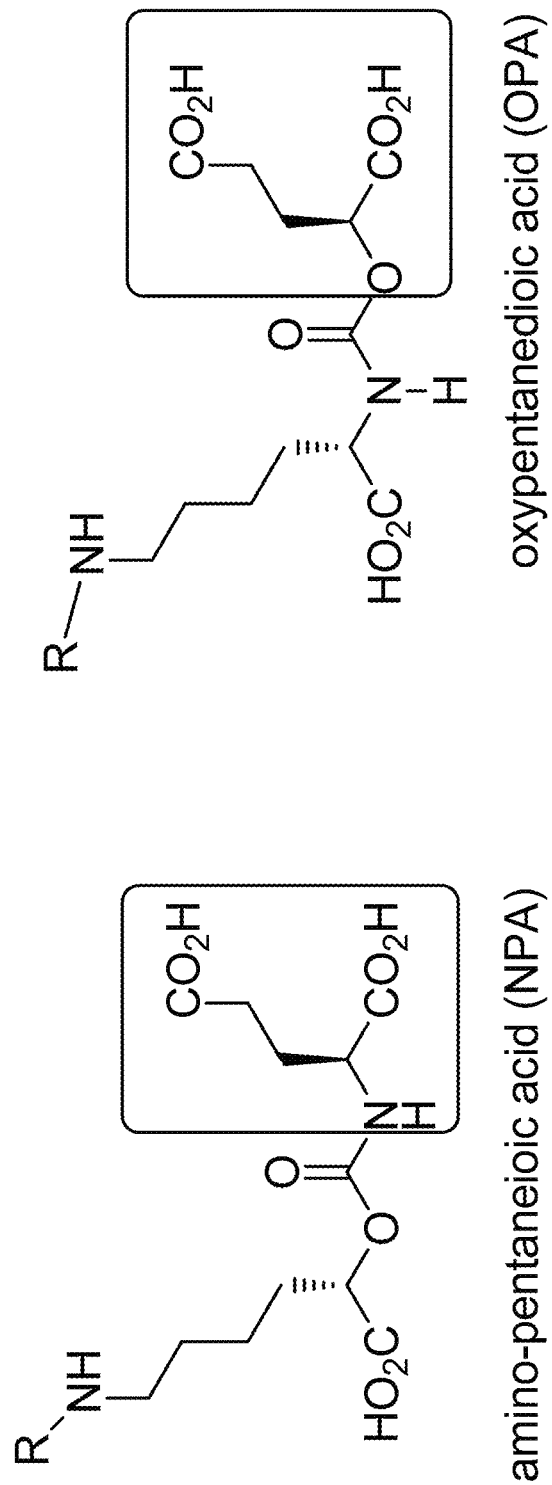
Figure 3:
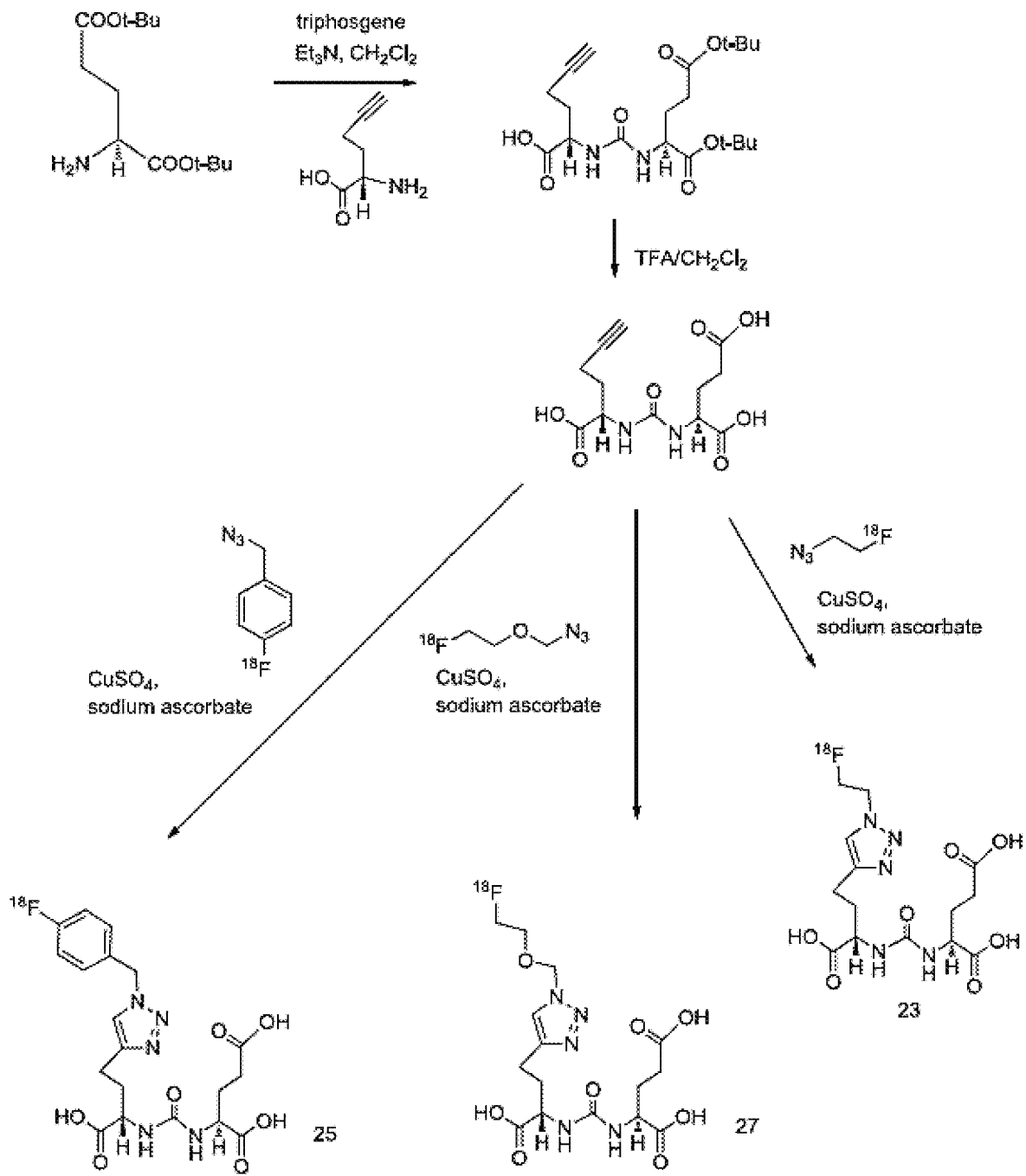
Figure 4:
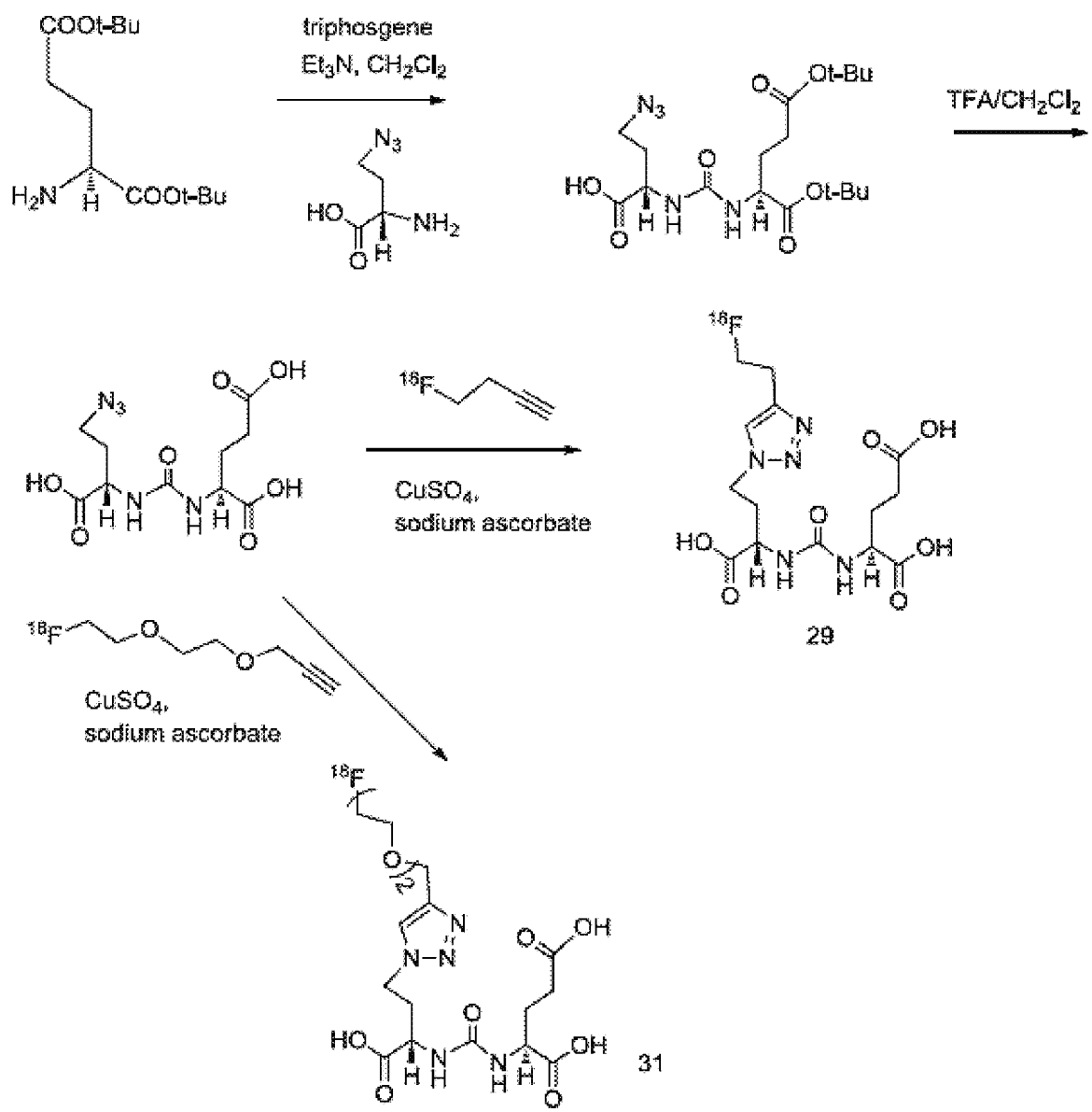
Figure 5:
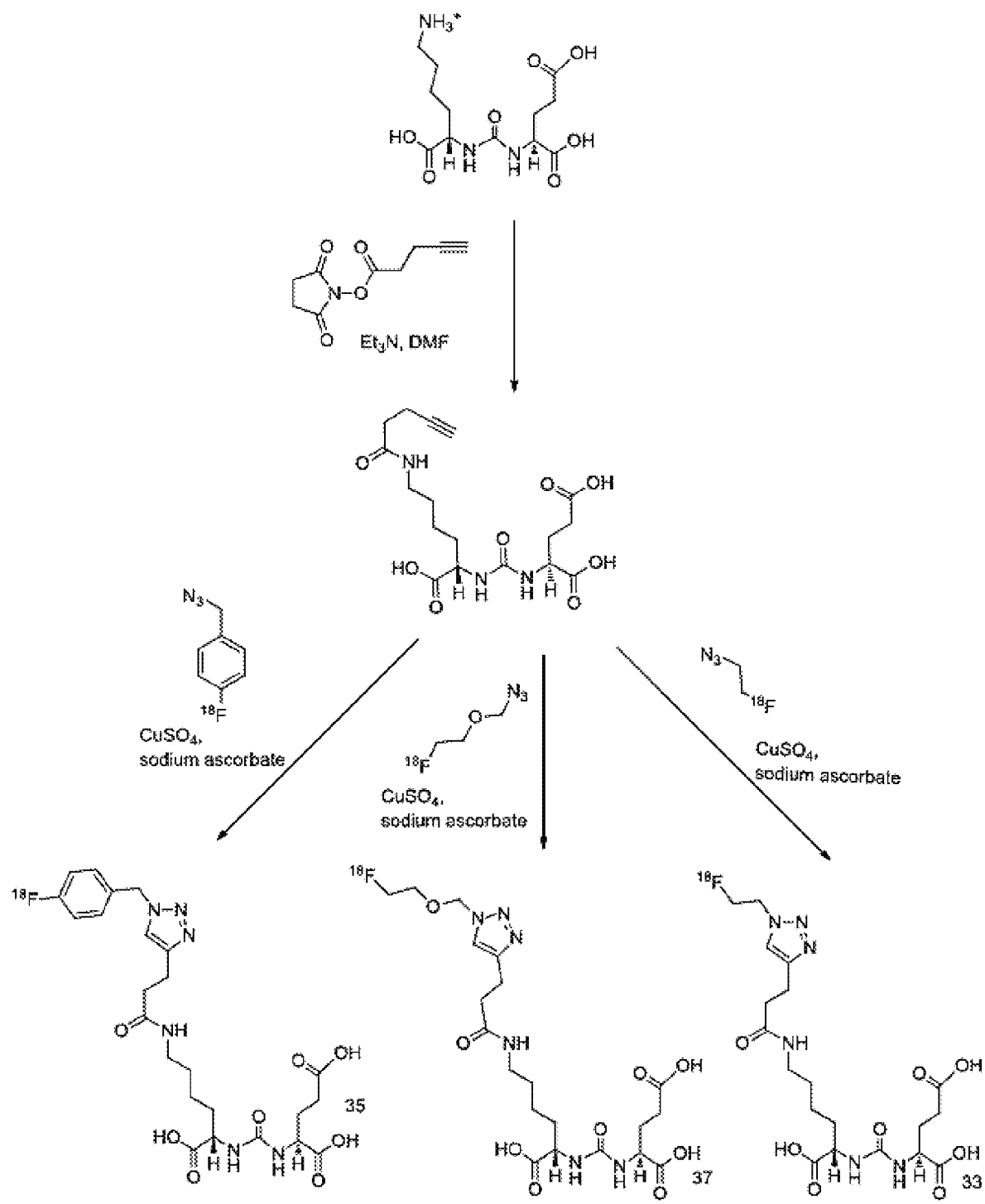
Figure 6:
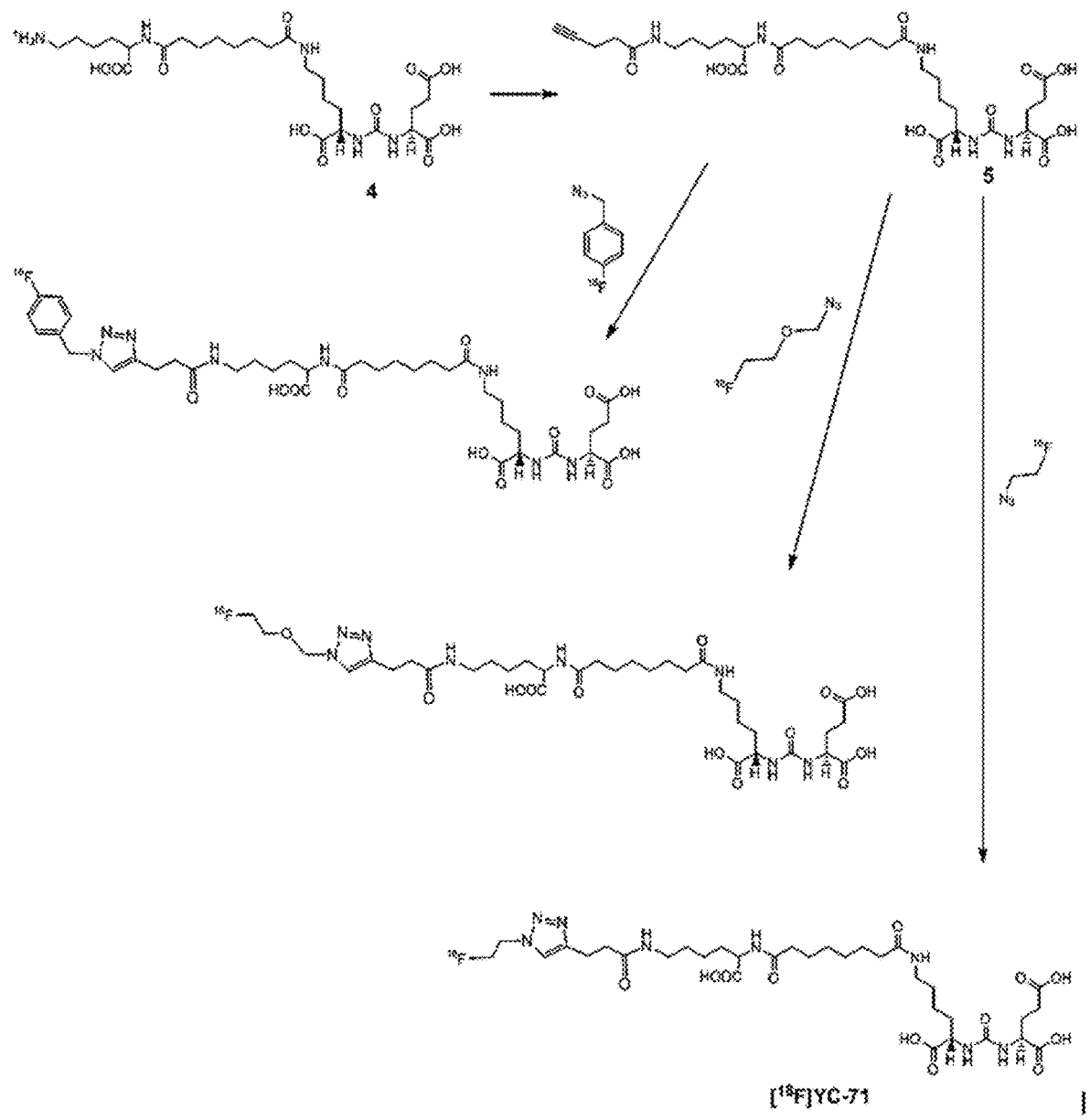
Figure 7:
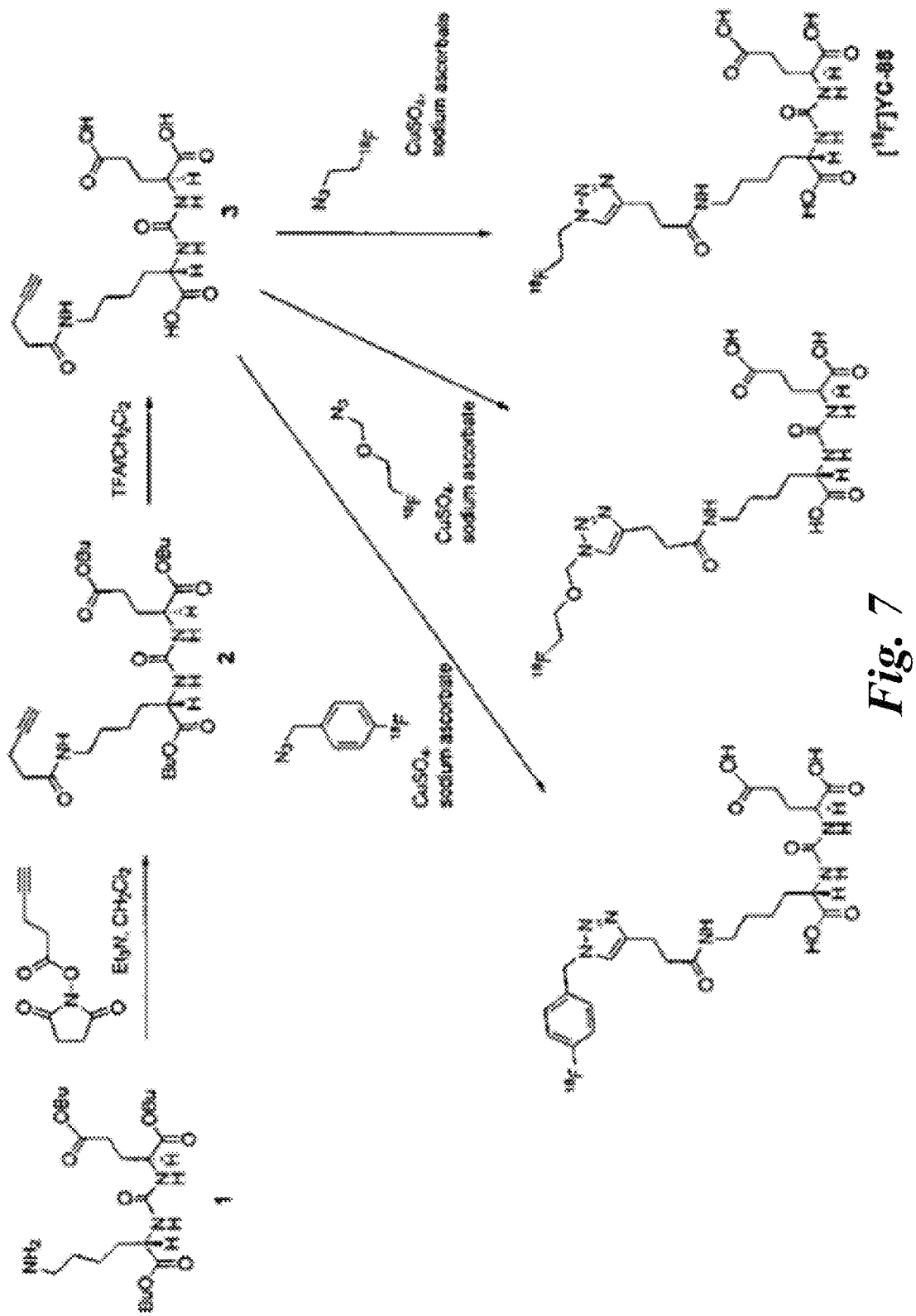
Figure 8:
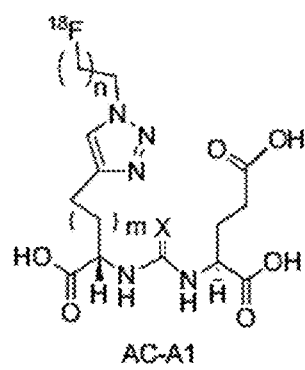
Figure 8:
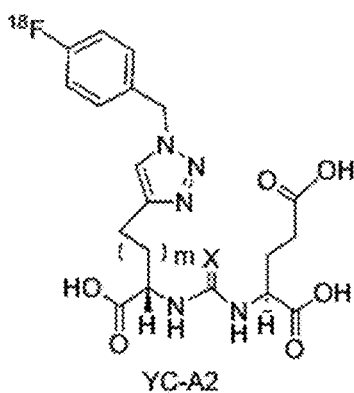
Figure 8:
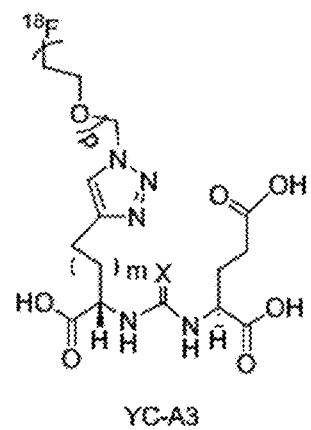
Figure 8:
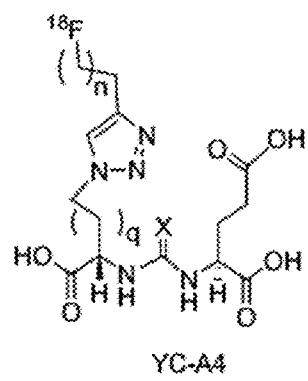
Figure 8:
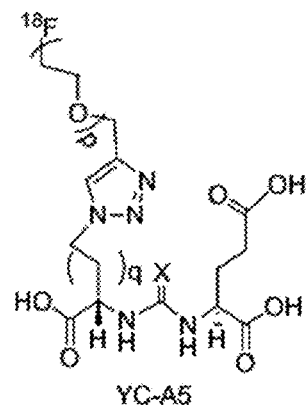
Figure 8:
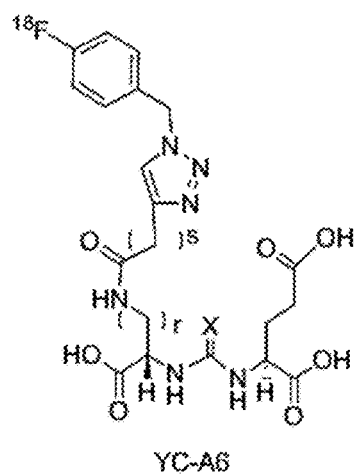
Figure 8:
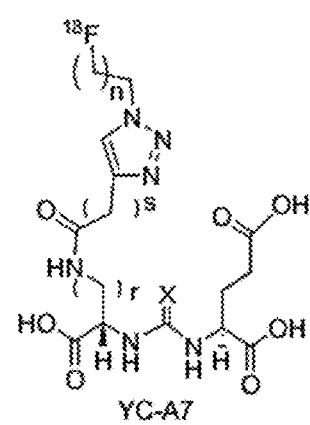
Figure 8:
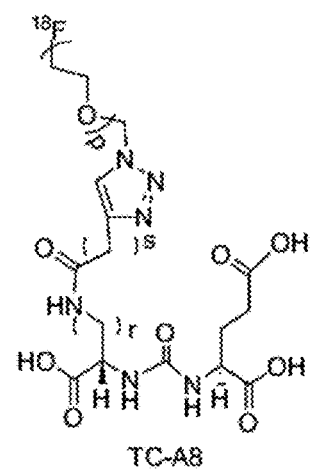
Figure 9:
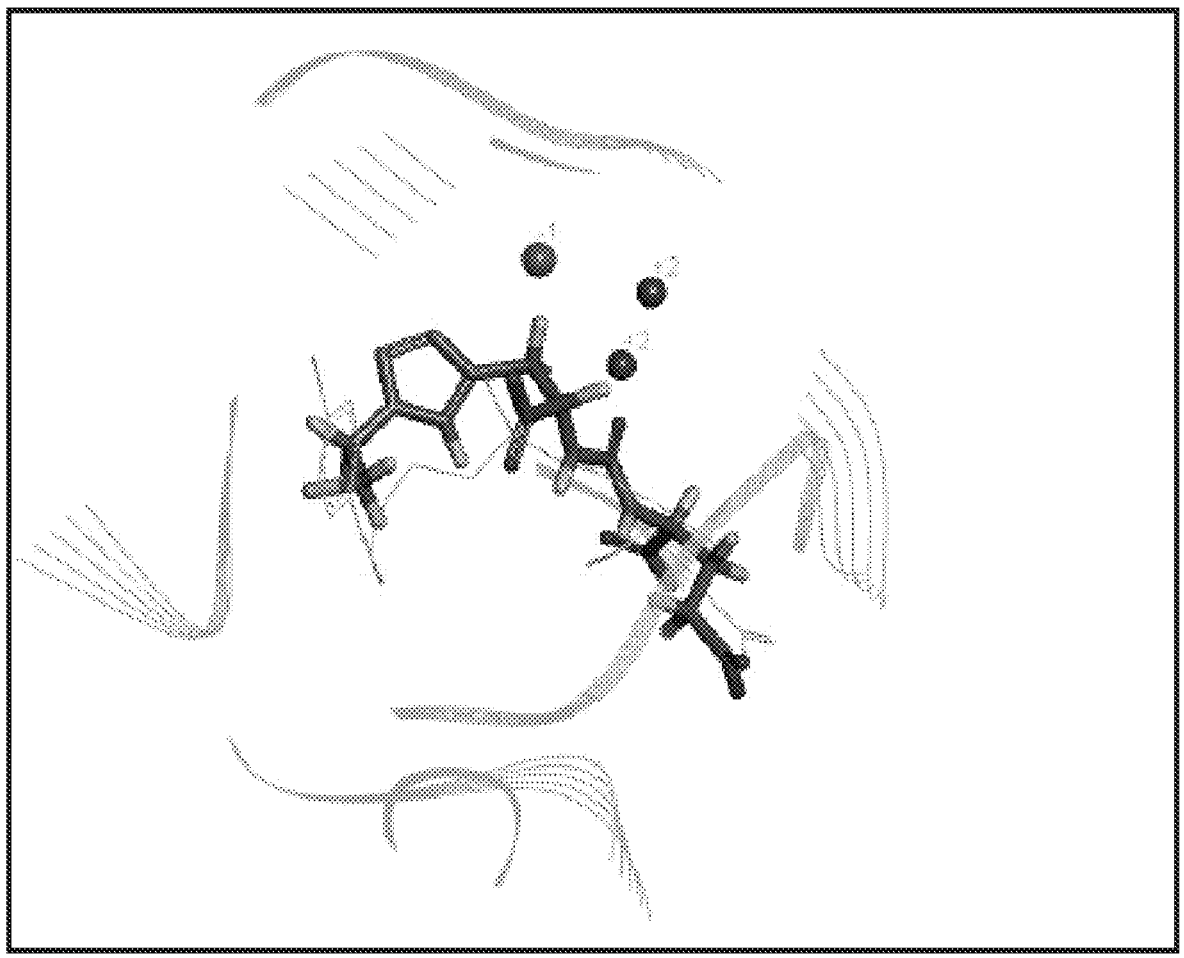
Figure 11:
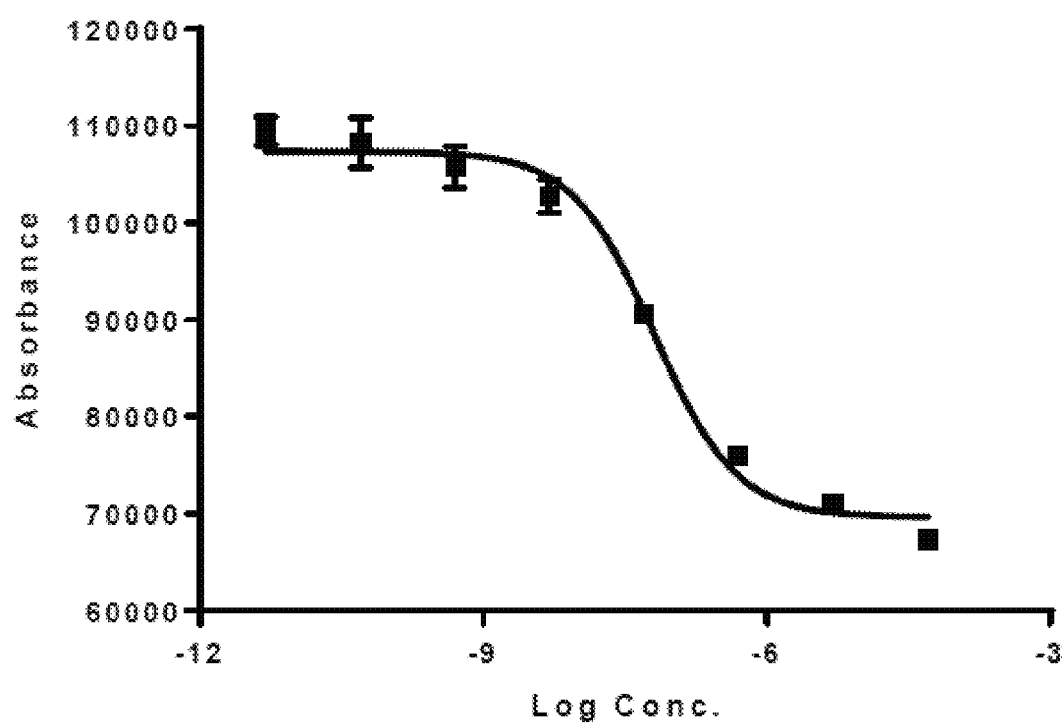
Figure 12:
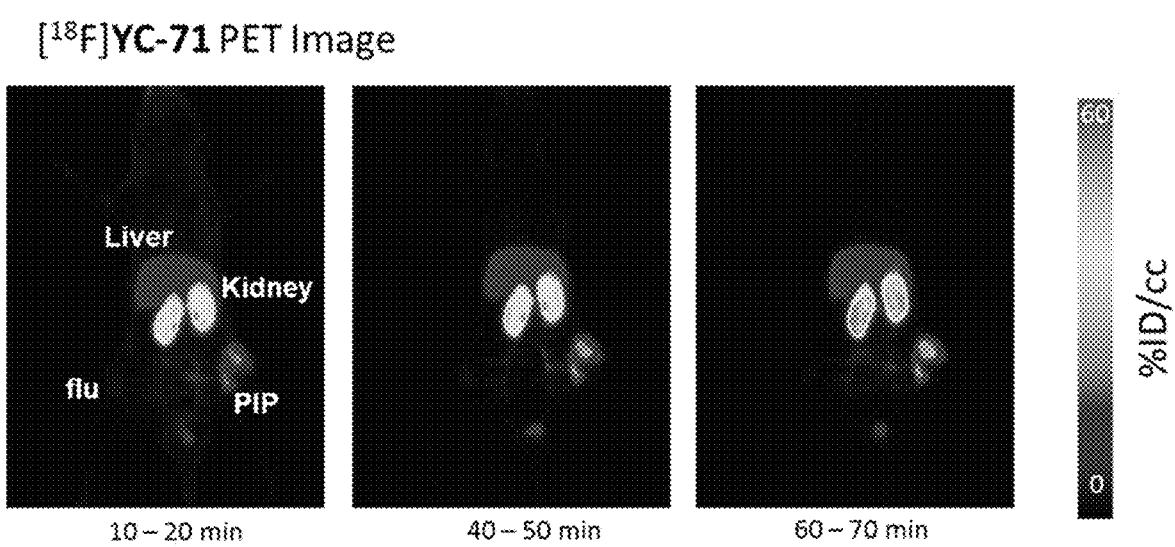
Figure 13:
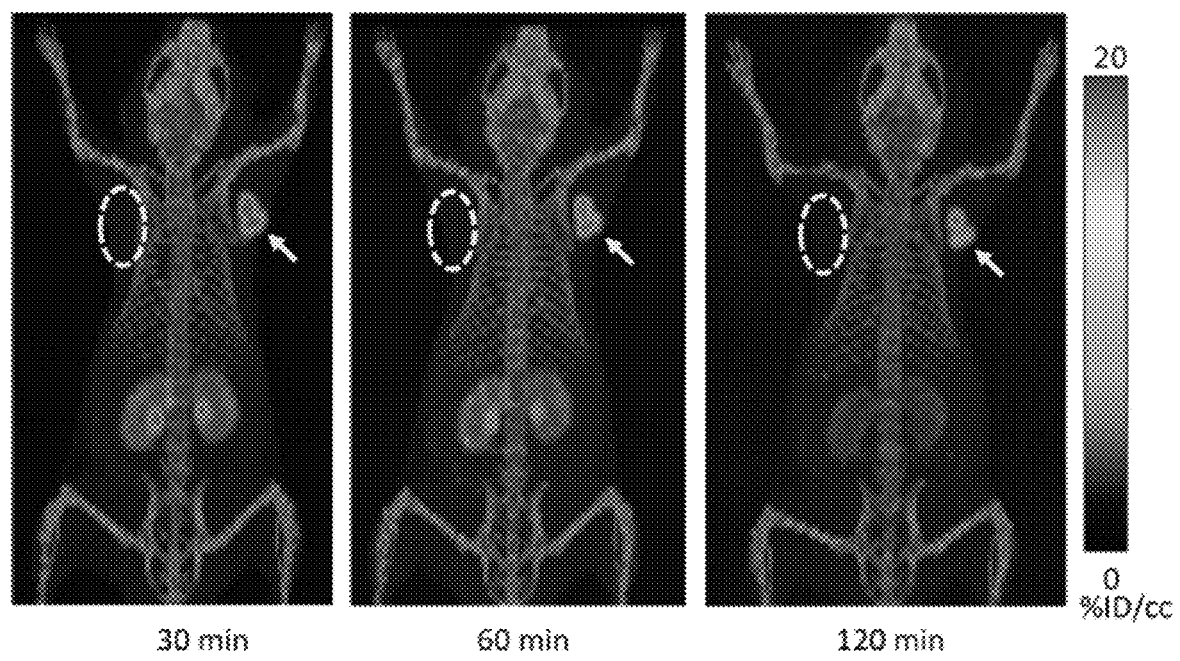
Figure 14:
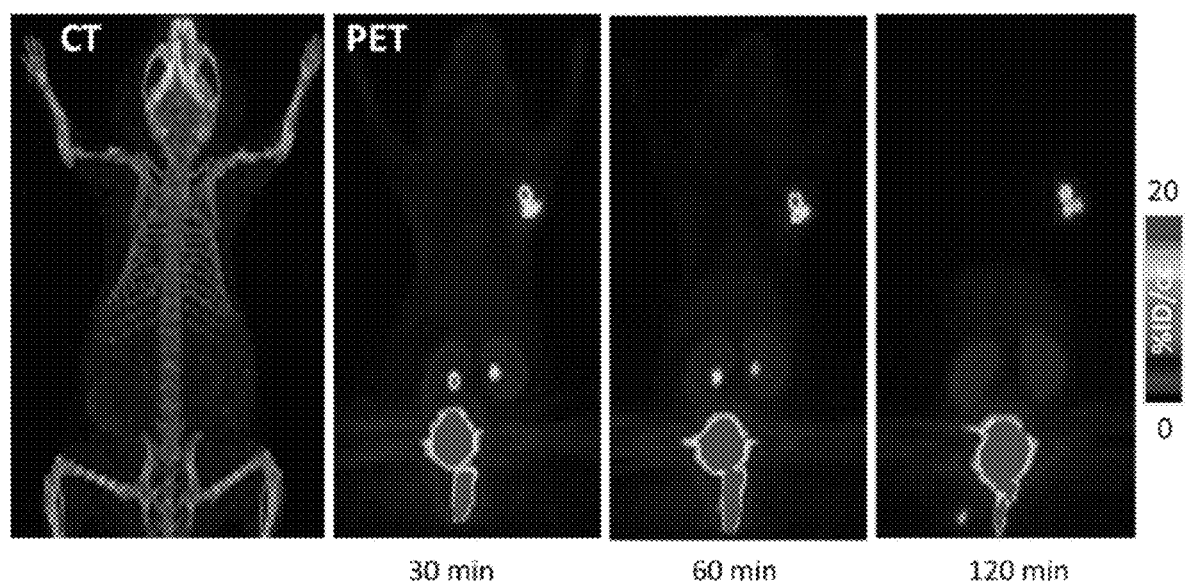

Having thus described the presently disclosed subject matter in general terms, reference will now be made to the accompanying Figures, which are not necessarily drawn to scale, and wherein:

FIG. 1A and FIG. 1B show (A) urea based scaffolds including the lysine-glutamate urea 1, cysteine-glutamate urea 2, and glutamate-glutamate urea 3; (B) shows examples of previously reported radiolabeled urea-based agents (prior art);

FIG. 2 shows two representative lysine-carbamate scaffolds: oxypentanedioic acid (OPA) corresponds to a carbamate scaffold and amino-pentanedioic acid (NPA) corresponds to a so-called "reverse" carbamate scaffold;

FIG. 3 is a synthesis scheme for the presently disclosed PSMA targeted radiolabeled triazole conjugated ureas, without a lysine suberate linker, developed through click chemistry, wherein the alkyne group is present on the urea moiety before azide-alkyne cycloaddition;

FIG. 4 is a synthesis scheme for the presently disclosed PSMA targeted radiolabeled triazole conjugated ureas, without a lysine suberate linker, developed through click chemistry, wherein the azide group is present on the urea moiety before azide-alkyne cycloaddition;

FIG. 5 is a synthesis scheme for the presently disclosed PSMA targeted radiolabeled triazole conjugated ureas, without a lysine suberate linker, developed through click chemistry, wherein the alkyne group is present on the urea moiety before azide-alkyne cycloaddition;

FIG. 6 is a synthesis scheme for the presently disclosed PSMA targeted radiolabeled triazole conjugated ureas, with a lysine suberate linker, developed through click chemistry, wherein the alkyne group is present on the urea moiety before azide-alkyne cycloaddition;

FIG. 7 is a three-step synthesis scheme for the presently disclosed PSMA targeted radiolabeled triazole conjugated ureas, without a lysine suberate linker, developed through click chemistry, wherein the alkyne group is present on the urea moiety before azide-alkyne cycloaddition;

FIG. 8 shows examples of representative presently disclosed terminal click urea and thiourea compounds;

FIG. 9 shows the correctly aligned docked pose for a terminal click urea derivative against 3D7H, overlaid over co-crystallized ligand, DCIBzl. This pose also was predicted by Libdock (Accelrys; San Diego, Calif.);

FIG. 10A, FIG. 10B, FIG. 10C, FIG. 10D, FIG. 10E, and FIG. 10F show the comparison of selected tissue uptake of [$^{18}$F]YC-88 and [$^{18}$F]DCFPyL in male NOD-SCID mice (n=3 to 4 per group) bearing both PSMA$^+$ PC3 PIP and PSMA$^-$ PC3 flu tumors: (A) PSMA$^+$ PC3 PIP tumor; (B) PSMA$^-$ PC3 flu tumor; (C) kidney; (D) salivary gland; (E) liver; and (F) spleen. (*, P<0.05; , P<0.01; *, P<0.001; ****, P<0.0001);

FIG. 11 shows the $IC_{50}$ curve of YC-88 using a fluorescence-based NAALADase assay;

FIG. 12 shows a positron emission tomography (PET) image of a tumor bearing mouse with the radiolabeled [$^{18}$F]YC-71 compound. A mouse bearing both PC3 PIP and PC3 flu tumors was injected with 0.2 mCi of [$^{18}$F]YC-71. Images were acquired from 10-20 minutes, 40-50 minutes, and 60-70 minutes post-injection;

FIG. 13 shows PET-CT images representing the time course of radiochemical uptake after the administration of [$^{18}$F]YC-88; PSMA$^+$ PC3 PIP (arrow) and PSMA$^-$ PC3 flu (dotted oval) tumors are present in subcutaneous tissues posterior to opposite forearms; mice were injected with 0.36 mCi (13.3 MBq) of [$^{18}$F]YC-88 at time 0; bladder activity was very high and cropped to improve the dynamic range of the display and enhance the visualization of radiochemical uptake in tumors and kidneys; the corresponding raw images are shown in FIG. 14; and FIG. 14 shows raw images of PET with [$^{18}$F]YC-88, including bladder activity.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Triazole Conjugated Ureas, Thiourea-Based, Carbamate, and "Reversed" Carbamates for Positron Emission Tomography Imaging of PSMA 1,3-Dipolar cycloadditions, commonly known as "click" reactions, both copper catalyzed and copper free, are being utilized in radiochemistry due to their mild reaction conditions, rapidity, reliability, high yield, and selectivity (Mamat et al., *Mini-Rev. Org. Chem.* 2009). The most common version of click chemistry used in small molecules is the copper catalyzed azide-alkyne cycloaddition to yield the triazole moiety. To this end, many $^{18}$F-azides and $^{18}$F-alkynes have been synthesized and used in radiolabeling (Glaser and Robins, *Journal of Labelled Compounds and Radiopharmaceuticals* 2009).

The presently disclosed subject matter provides triazole conjugated urea-based, thiourea-based, carbamate, and "reversed" carbamate scaffolds that have high binding affinity to PSMA and that are synthesized using click chemistry. These scaffolds can be radiolabeled and used to image cells and tumors that express PSMA. The urea-based scaffolds include: the lysine-glutamate urea 1, cysteine-glutamate urea 2, and glutamate-glutamate urea 3 as disclosed on FIG. 1A. The carbamate based scaffolds include: oxypentanedioic acid (OPA), corresponding to a carbamate scaffold and amino-pentanedioic acid (NPA), corresponding to a "reverse" carbamate scaffold as disclosed on FIG. 2.

Two families of triazole conjugated ureas are described herein: compounds having a lysine-suberate linker, as disclosed, for instance, in FIG. 6, or those compounds not having a lysine-suberate linker, as disclosed, for instance, in FIG. 3. Primary modeling studies using the Libdock module of the Discovery Studio 3.1 suite, as shown in FIG. 9, indicate that the presently disclosed structures can be aligned properly within the binding site of PSMA in a similar fashion to reference urea-based compounds. Another family of triazole conjugated carbamates and "reverse" carbamates having a lysine-suberate linker also is described herein.

In some embodiments, the presently disclosed subject matter provides triazole conjugated urea-based and thiourea-based scaffolds as disclosed in FIG. 8, as well as carbamate and "reversed" carbamate scaffolds as disclosed in FIG. 2. Versatile intermediates for triazole conjugated urea-based, thiourea-based, carbamate, and "reversed" carbamate scaffolds can be functionalized in one or two steps to provide PET imaging agents. Further, it is possible that the radiofluorination of carbamates via triazoles may be easier, and more amenable to automation for large scale radiosynthesis for regional distribution and thereby more commercially viable than other radiofluorination methods.

In other embodiments, the presently disclosed subject matter provides a one pot synthesis of the urea-based PSMA inhibitor [$^{18}$F]YC-88 from [$^{18}$F]fluoroethyl azide and the corresponding alkyne precursor.

In yet other embodiments, the presently disclosed subject matter also provides a one pot synthesis of the urea-based PSMA inhibitor [$^{18}$F]YC-88 using an automated radiofluorination module.

A. Compounds of Formula (I)

Accordingly, in some embodiments, the presently disclosed subject matter provides a compound of formula (I):

In particular embodiments, R is selected from the group consisting of:

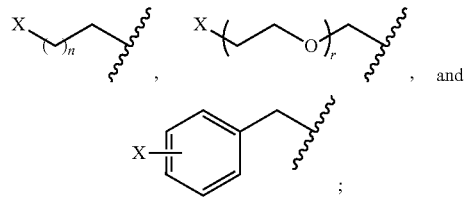

, and wherein n and r are each an integer independently selected from the group consisting of 0, 1, 2, 3, 4, 5, 6, 7, 8, 9, and 10; X is selected from the group consisting of fluorine, bromine, iodine, astatine, a radioisotope of fluorine, a radioisotope of bromine, a radioisotope of iodine, and a radioisotope of astatine. In more particular embodiments, X is selected from the group consisting of F-18, F-19, Br-75, Br-76, Br-77, Br-80m, Br-83, Br-80, I-123, I-124, I-125, I-131, At-211. In yet further particular embodiments, X is $^{18}$F.

In yet even more particular embodiments, the compound of Formula (I) is selected from the group consisting of:

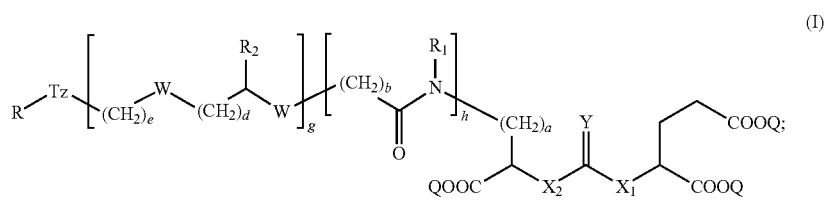

(I)

wherein: Z is tetrazole or $CO_2Q$; Q is H or a protecting group; Y is O or S; $X_1$ and $X_2$ are each independently selected from the group consisting of O and NH; a, b, d, and e are each an integer independently selected from the group consisting of 0, 1, 2, 3, 4, 5, 6, 7, 8, 9, and 10; g and h are each independently 0 or 1; each $R_1$ is independently H or $C_1$-$C_4$ alkyl;

each $R_2$ is independently H or COOH; each W is independently selected from the group consisting of —C(=O)—$NR_2$—, —$NR_2$—C(=O)—, —$NR_2$—C(=O)—$NR_2$—, —$NR_2$—C(=S)—$NR_2$—, —$NR_2$—C(=O)—O—, —O—C(=O)—$NR_2$—, —O—C(=O)—, or —C(=O)—O—; Tz is a triazole selected from the group consisting of:

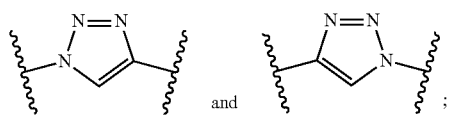

and R is selected from the group consisting of substituted and unsubstituted alkyl, substituted and unsubstituted aryl, substituted and unsubstituted alkoxyl, each of which can comprise a radioactive isotope suitable for imaging or a halogen; and stereoisomers and pharmaceutically acceptable salts thereof.

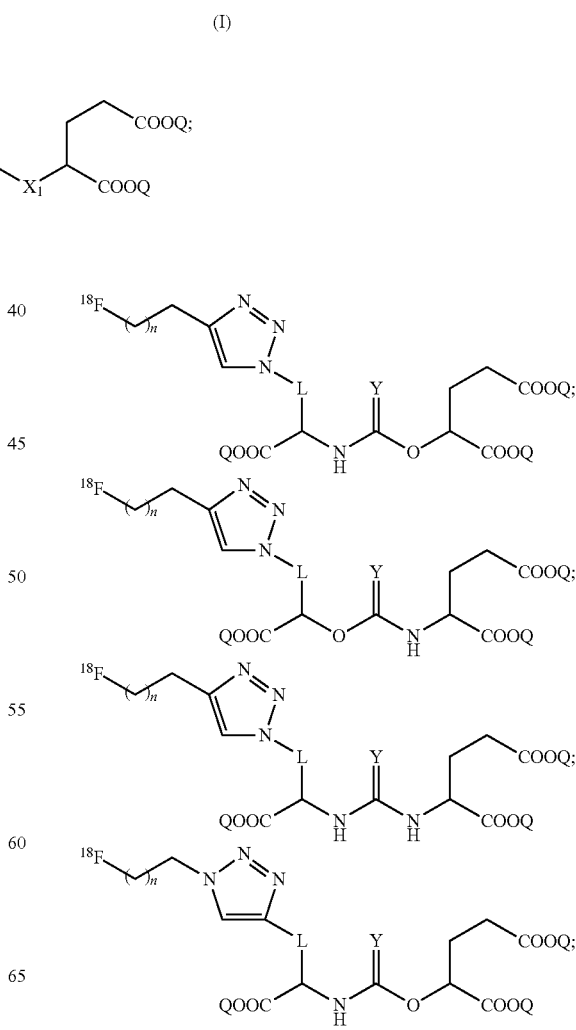

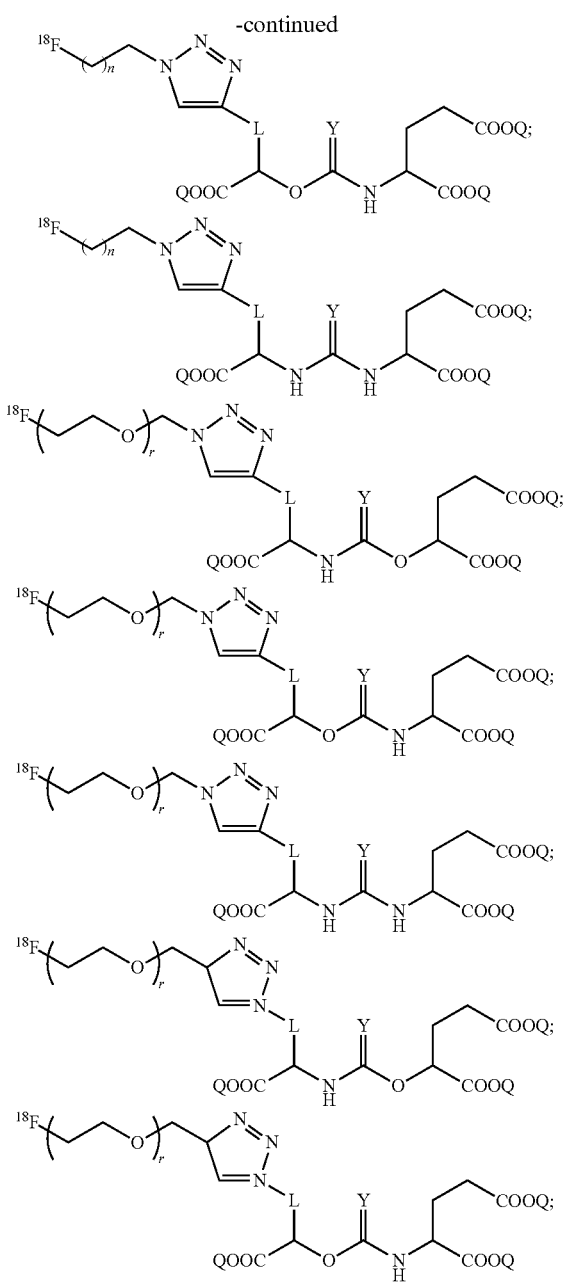
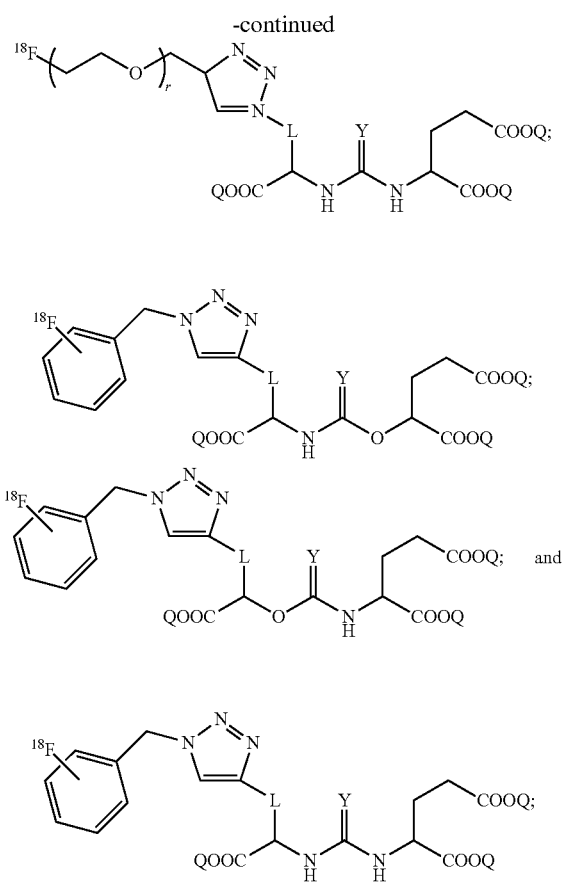
wherein L is:
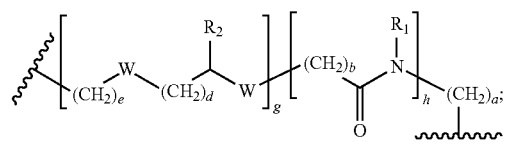
and wherein a, b, d, e, g, $R_1$, W, and $R_2$ are defined hereinabove.
In further embodiments, the compound of formula (I) is selected from the group consisting of:
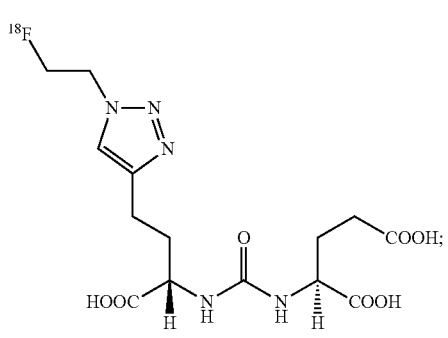
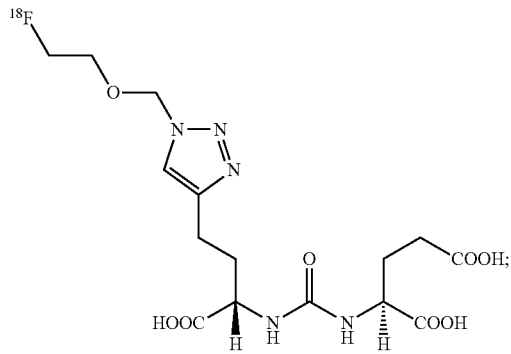

11
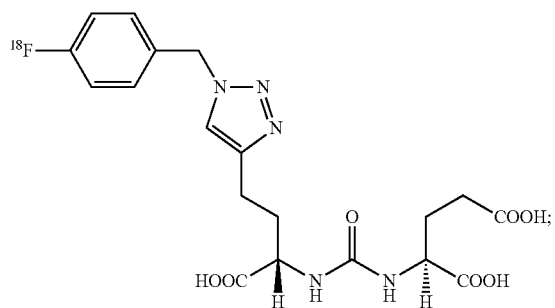
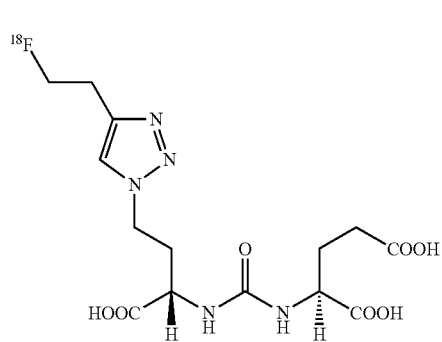
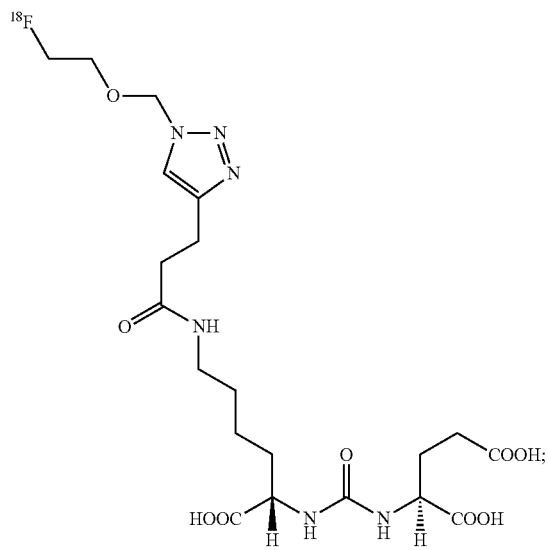
12
-continued
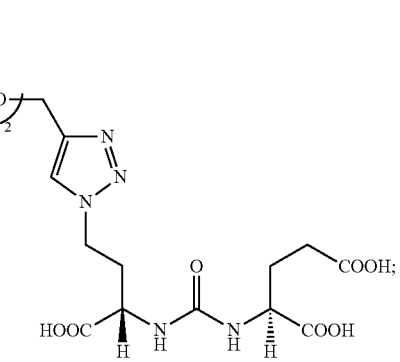
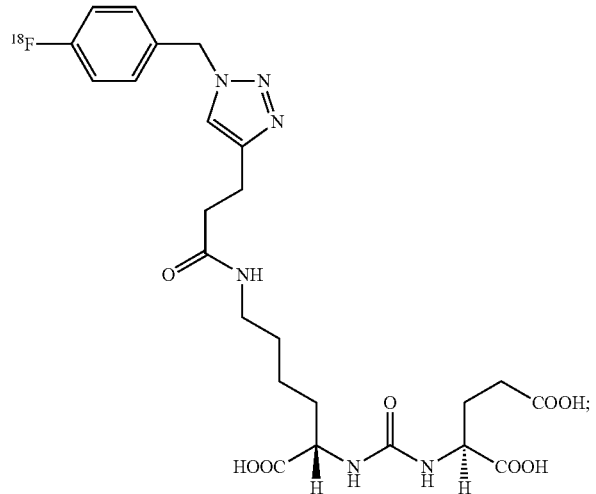
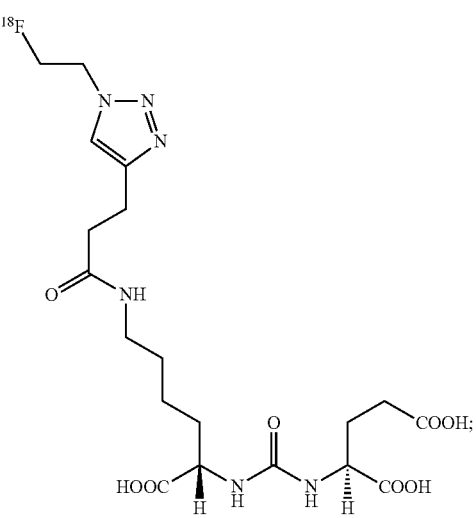

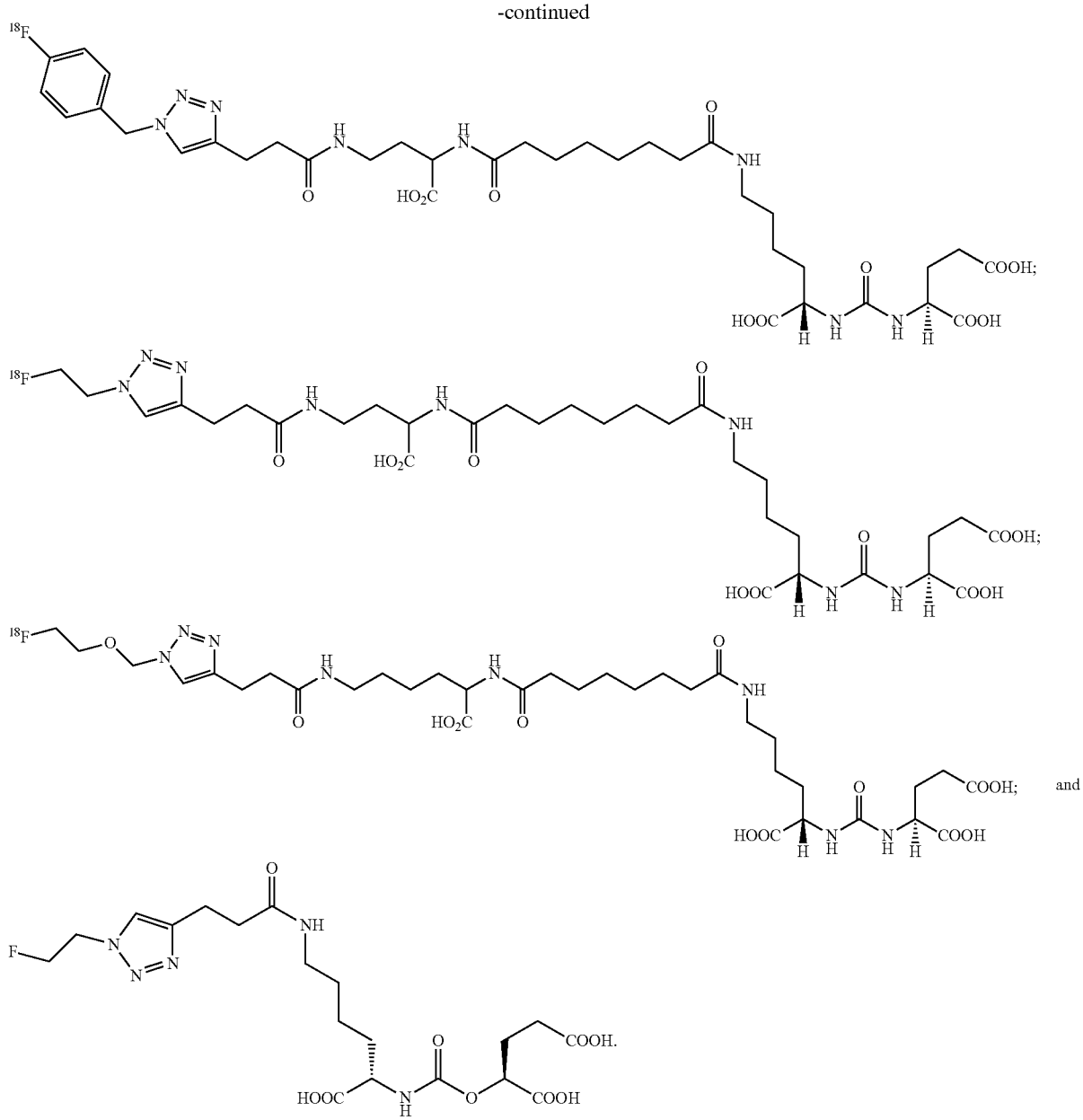
In yet more certain embodiments, the compound of formula (I) is selected from the group consisting of:
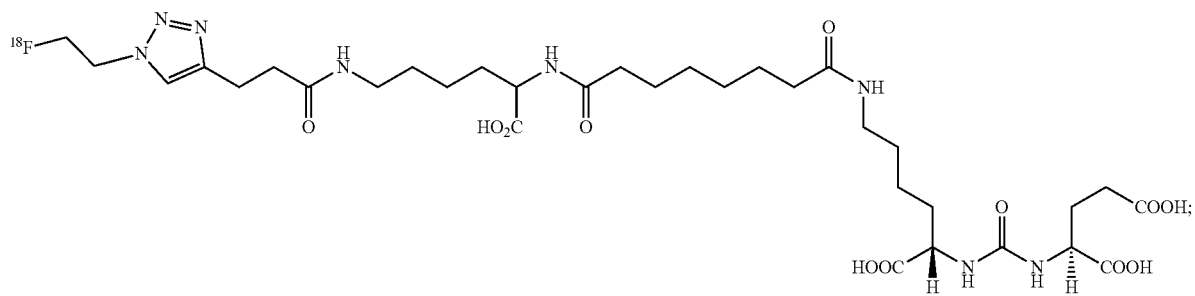
[18]YC-71

-continued

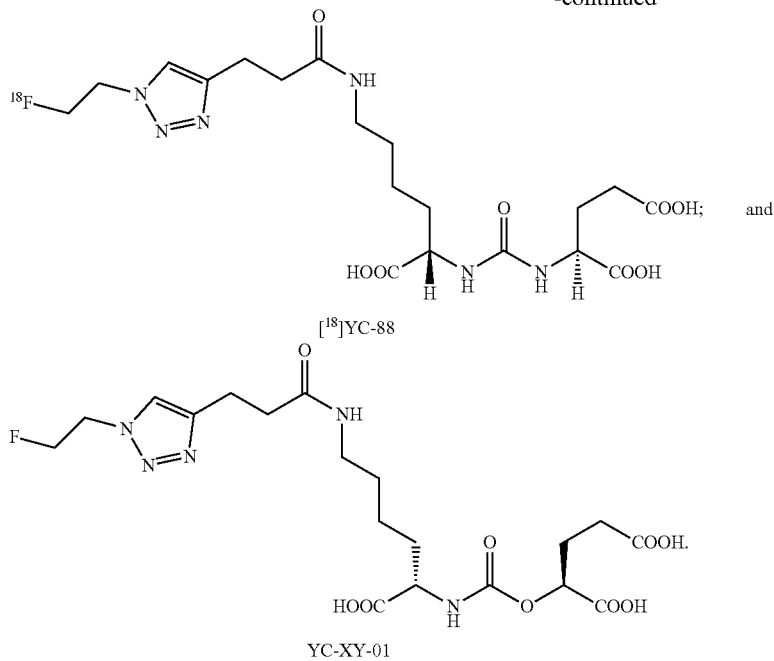

[¹⁸]YC-88

YC-XY-01

B. Methods of Using Compounds of Formula (I) for Imaging a PSMA-Expressing Tumor or Cell In some embodiments, the presently disclosed subject matter provides a method for imaging one or more prostate-specific membrane antigen (PSMA)-expressing tumors or cells, the method comprising contacting the one or more tumors or cells with an effective amount of a compound of formula (I), and making an image, wherein the compound of formula (I) comprises a radioactive isotope suitable for imaging.

"Contacting" means any action which results in at least one compound comprising the imaging agent of the presently disclosed subject matter physically contacting at least one PSMA-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s). In some embodiments, the tumor or cell is found in vitro, in vivo, or ex vivo.

By "making an image," it is meant using PET to form an image of a cell, tissue, tumor, part of body, and the like. The presently disclosed methods may include one or more radioactive isotopes capable of emitting radiation suitable for detection with PET. In some embodiments, the imaging agent is capable of generating at least a 2:1 target to background ratio of radiation intensity, or more preferably about a 5:1, about a 10:1 or about a 15:1 ratio of radiation intensity between target and background.

In certain embodiments, the one or more PSMA-expressing tumors or cells is selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In yet more certain embodiments, the one or more PSMA-expressing tumors or cells is a prostate tumor or cell.

In some embodiments, the one or more PSMA-expressing tumors or cells is in vitro, in vivo, or ex vivo. In particular embodiments, the one or more PSMA expressing tumors or cells is present in a subject.

In some embodiments, the tumor or cell is found in a subject. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment that is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film related factors. Optimization of such factors is well within the level of skill in the art.

It is preferable to have the compound comprising the imaging agent to localize to the tumor or cell quickly after administration so as to minimize any side effects to the subject. Accordingly, in some embodiments, the compound comprising the imaging agent substantially localizes to the tumor or cell within about 60 minutes to about 240 minutes of administration and, in some embodiments, about 60 minutes. In other embodiments, the compound comprising the imaging agent substantially localizes to the tumor or cell within about 30 minutes of administration. In still other embodiments, the compound comprising the imaging agent substantially localizes to the tumor or cell within about 10 minutes of administration.

It also is preferable that the compounds of the presently disclosed subject matter are excreted from tissues of the body quickly to prevent prolonged exposure to the radiation of the radiolabeled compound administered to the patient. Typically compounds of the presently disclosed subject matter are eliminated from the body in less than about 24 hours. More preferably, compounds of the presently disclosed subject matter are eliminated from the body in less than about 16 hours, 12 hours, 8 30 hours, 6 hours, 4 hours, 2 hours, 90 minutes, or 60 minutes.

In some embodiments, the presently disclosed methods comprise clearance of the compound comprising the imaging agent from the tumor or cell in the subject. At least one advantage of the presently disclosed methods is that, in some embodiments, there is more rapid clearance of the compound comprising the imaging agent from the kidneys than from the tumor of the subject.

In some embodiments, the presently disclosed methods use compounds that are stable in vivo such that substantially all, e.g., more than about 50%, 60%, 70%, 80%, or 5 more preferably 90% of the injected compound is not metabolized by the body prior to excretion. In other embodiments, the compound comprising the imaging agent is stable in vivo.

A "tumor," as used herein, refers to all neoplastic cell growth and proliferation, whether malignant or benign, and all precancerous and cancerous cells and tissues.

In some embodiments, the tumor cells express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. Essentially all solid tumors express PSMA in the neovasculature. Therefore, methods of the presently disclosed subject matter can be used to image nearly all solid tumors including, but not limited to, lung, renal cell, glioblastoma, pancreas, bladder, sarcoma, melanoma, breast, colon, germ cell, pheochromocytoma, esophageal, and stomach tumors. Also, certain benign lesions and tissues including, but not limited to, endometrium, schwannoma and Barrett's esophagus, can be imaged according to the presently disclosed methods.

C. Methods of Synthesizing Compounds of Formula (I)

In some embodiments, the presently disclosed subject matter provides a one-pot method of synthesizing a radiofluorinated compound of formula (I), the method comprising: (i) radiofluorinating a compound selected from the group consisting of

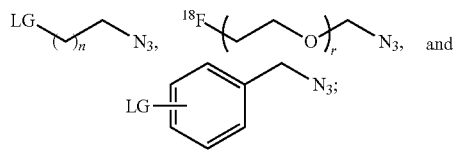

wherein LG is a leaving group; with [$^{18}$F]fluoride ion to form a radiofluorinated compound selected from the group consisting of

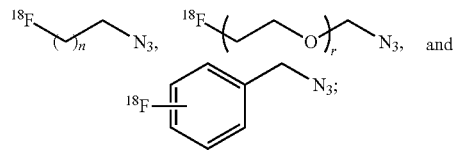

(ii) contacting the radiofluorinated compound (i) with copper (II) sulfate, sodium ascorbate, and a compound of formula (II):

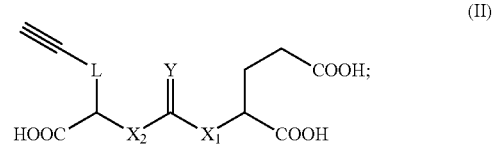

wherein L is

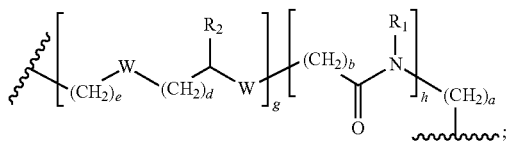

wherein a, b, d, e, g, $R_1$, W, and $R_2$ are defined hereinabove; Y is O or S; $X_1$ and $X_2$ are each independently selected from the group consisting of O and NH; to form a radiofluorinated compound of formula (I) in a reaction mixture; and (iii) purifying the radiofluorinated compound of formula (I) from the reaction mixture of step (ii) to provide a radiofluorinated compound of formula (I).

As used herein, a "leaving group" is a group that permits the compound bearing the leaving group combined with [$^{18}$F]fluoride ion to form a radiofluorinated compound via nucleophilic heteroaromatic substitution reaction. In some embodiments, the leaving group is selected from the group consisting of but not limited to bromide (—Br), iodide (—I), triflate (—OTf), tosylate (—OTs), and mesylate (—OMs).

In some embodiments, step (i) and step (ii) are each carried out in dimethylformamide (DMF). In some embodiments, step (i) and step (ii) are each carried out at a temperature having a range from about 30° C. to about 150° C. In certain embodiments, the temperature is about 50° C. In some embodiments, step (i) and step (ii) are each carried out for between about one minute to about 10 minutes. In certain embodiments, step (i) and step (ii) are each carried out for about 5 minutes. In some embodiments, the specific activity of [$^{18}$F]YC-88 after purification is at least about 300 Ci/mmol. In some embodiments, the specific activity of [$^{18}$F]YC-88 after purification is at least about 2,400 Ci/mmol.

In other embodiments, the presently disclosed subject matter provides a method of synthesizing radiofluorinated compound of formula (I); the method comprising: (i) synthesizing a radiolabeled compound of formula (III') by reacting a compound of formula (II') with [$^{18}$F]fluoride ion;

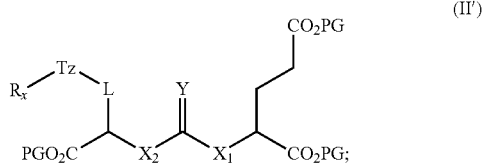
(II')

wherein $R_x$ is selected from the group consisting of:

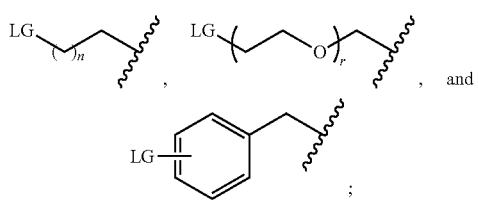

wherein each PG is a protecting group of an ester moiety that is removable by treatment with phosphoric acid, and LG is a leaving group;

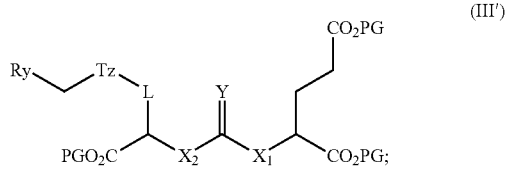
(III')

wherein Ry is selected from the group consisting of:

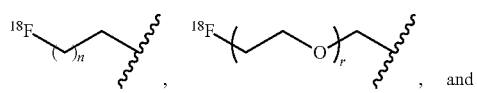
, and

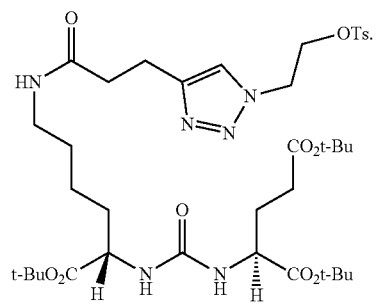
;

(ii) cleaving the protecting groups (PG) of the compound of formula (III') to obtain form a radiofluorinated compound of formula (I) in a reaction mixture; and (iii) purifying the radiofluorinated compound of formula (I) from the reaction mixture of step (ii) to provide a radiofluorinated compound of formula (I).

As used herein, a "protecting group" is a chemical substituent which can be selectively removed by readily available reagents which do not attack the regenerated functional group or other functional groups in the molecule. Suitable protecting groups may be found, for example in Wutz et al. ("Greene's Protective Groups in Organic Synthesis, Fourth Edition," Wiley-Interscience, 2007). Protecting groups for protection of an ester moiety, as described by Wutz et al. (pages 533-643), are used in certain embodiments. Specific examples of protecting groups include but are not limited to, benzyl, p-methoxybenzyl (PMB), tertiary butyl (tertbutyl, or t-butyl), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), tbutyldimethylsilyl (TBDMS), and triphenylmethyl (trityl, Tr).

In certain embodiments, the compound of formula (III') is:

In other embodiments, step (i) and step (ii) are performed in one reactor.

In certain embodiments, the radiosynthesis is automated by use of an radiofluorination module (RFM). In certain embodiments, the RFM further comprises a thermal heating cavity.

In some embodiments the [$^{18}$F]fluoride ion from step (i) is dried.

In other embodiments, the [$^{18}$F] fluorination reaction described in step (i) is carried out at a temperature having a range from about 30° C. to about 150° C. In certain embodiments, the temperature is about 50° C.

In some embodiments, the [$^{18}$F] fluorination reaction described in step (i) is carried out for between about 6 minutes to about 20 minutes. In certain embodiments, the [$^{18}$F] fluorination reaction described in step (i) is carried out for about 12 minutes.

In some other embodiments, the [$^{18}$F] fluorination reaction described in step (i) is carried out in acetonitrile ($CH_3CN$).

In some embodiments, the deprotection with phosphoric acid is performed at a temperature having a range from about 30° C. to about 55° C. In certain embodiments, the temperature is about 45° C.

In some embodiments, the deprotection with phosphoric acid is carried out for between about one minute to about 10 minutes. In certain embodiments, the deprotection with phosphoric acid is carried out for about 6 minutes.

In some embodiments, the method further comprises adjusting the pH of the reaction mixture of step (ii) after the deprotection with phosphoric acid to a pH of between about 2 to about 2.5. In certain embodiments, the pH of the reaction mixture is adjusted by adding sodium hydroxide and sodium dihydrogen phosphate buffer.

In some embodiments, the radiofluorinating step comprises:
(a) trapping [$^{18}$F]fluoride ion in a cartridge;
(b) eluting the cartridge with a solution of tetrabutylammonium base salt to release the [$^{18}$F]fluoride ion trapped in the cartridge;
(c) drying the eluate comprising the [$^{18}$F]fluoride ion to form dried [$^{18}$F]fluoride ion;
(d) adding a solution of the compound of formula (III') to the dried [$^{18}$F]fluoride ion. In some embodiments, the cartridge is an anion exchange chromatographic cartridge. In some embodiments, the cartridge is pre-conditioned by washing with high purity water prior to trapping [$^{18}$F]fluoride ion in the cartridge.

In some embodiments, the [$^{18}$F]fluoride ion from step (c) is dried.

In some embodiments, the eluate of step (c) comprising the [$^{18}$F]fluoride ion is dried at a temperature of between about 80° C. to about 150° C. In some embodiments, the temperature is about 110° C. In some embodiments, the eluate of step (c) comprising the [$^{18}$F]fluoride ion is dried under nitrogen flow. In some embodiments, the drying is performed for about 50 seconds to about 300 seconds.

In some embodiments, the drying is performed for about 150 seconds. In some embodiments, CH$_3$CN is added to the dried [$^{18}$F]fluoride ion for further drying. In some embodiments, the RFM or automated radiochemistry synthesizer, or reaction portion thereof, is cleaned with dilute nitric acid, washed with water and dried at about 80° C. overnight prior to the synthesis.

In some embodiments, the purifying is performed by liquid chromatography. In some embodiments, the solution comprising the radiofluorinated compound of formula (I) is eluted from a C18 column with an elution solution comprising methanol and sodium dihydrogen phosphate.

In some embodiments, the methanol and sodium dihydrogen phosphate in the elution solution is 15:85 methanol: 0.01M sodium dihydrogen phosphate at pH 2.2.

In some embodiments, the yield of the radiofluorinated compound of formula (I) after purification is at least 5%.

II. Definitions

A. Chemical Definitions

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$5—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH—CH═CH—; —CH═CH—CH$_2$—; —CH$_2$CH$_2$CH$_2$CH$_2$—, —CH$_2$CH═CHCH$_2$—, —CH$_2$C≡CCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

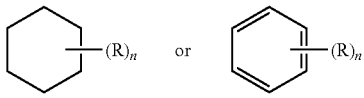

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

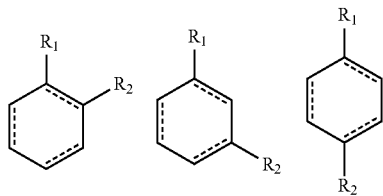

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ～～～ ) denotes the point of attachment of a moiety to the remainder of the molecule.

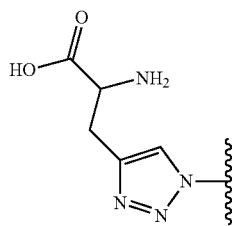 [SMILES: *n1cc(CC(N)C(=O)O)nn1]

Substituents bearing two broken bonds, such as the example shown below, means that the orientation of the atoms is as-indicated, left to right and should be inserted into a molecule in the orientation shown. No additional methylene ($CH_2$) groups are implied unless specifically indicated.

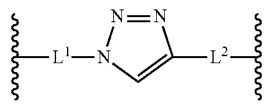

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', —NR'R", —SR', -halogen, —SiR'R"R'", —OC(O)R', —C(O)R', —$CO_2$R', —C(O) NR'R", —OC(O)NR'R", —NR"C(O)R', —NR'—C(O) NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such groups. R', R", R'" and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —$CO_2$R', —C(O)NR'R", —OC(O)NR'R", —NR"C(O)R', —NR'—C(O)NR"R'", —NR"C(O)OR', —NR—C (NR'R"R'")=NR"", —NR—C(NR'R")=NR'"—S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocyclic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-

$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

The term ureido refers to a urea group of the formula —NH—CO—$NH_2$.

Unless otherwise explicitly defined, a "substituent group," as used herein, includes a functional group selected from one or more of the following moieties, which are defined herein:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like also can be present in the compounds described herein, and all such stable isomers are contemplated in the presently disclosed subject matter. Cis and trans geometric isomers of the compounds of the presently disclosed subject matter are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

As used herein, a "protecting group" is a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid. Specific examples of protecting groups include but are not limited to, benzyl, p-methoxybenzyl (PMB), tertiary butyl ($^t$Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

ii. Pharmaceutical Salts

The compounds of the present disclosure may exist as pharmaceutically acceptable salts. The term "pharmaceutically acceptable salts" is meant to include salts of active compounds which are prepared with relatively nontoxic acids or bases, depending on the particular substituent moieties found on the compounds described herein. Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrates, (e.g. (+)-tartrates, (−)-tartrates or mixtures thereof including racemic mixtures), or teoclate. These salts may be prepared by methods known to those skilled in art. Other pharmaceutically acceptable salts may be found in, for example, Remington: The Science and Practice of Pharmacy (20$^{th}$ ed.) Lippincott, Williams & Wilkins (2000).

Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like.

Also included are salts of amino acids such as arginate and the like, and salts of organic acids like glucuronic or galactunoric acids and the like, see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

iii. Pharmaceutical Compositions

The compounds disclosed herein can be formulated into various compositions, for use in diagnostic and imaging methods. Generally, a pharmaceutical composition comprises an effective amount (e.g., a detectably effective amount) of a compound described hereinabove.

A presently disclosed composition can be formulated as a pharmaceutical composition, which comprises a presently disclosed compound and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18[1] ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

One skilled in the art will appreciate that the particular formulation will depend, in part, upon the particular agent that is employed, and the chosen route of administration. Accordingly, there is a wide variety of suitable formulations of compositions of the presently disclosed subject matter.

One skilled in the art will appreciate that a suitable or appropriate formulation can be selected, adapted or developed based upon the particular application at hand. Dosages for presently disclosed compositions can be in unit dosage form. The term "unit dosage form" as used herein refers to physically discrete units suitable as unitary dosages for animal (e.g. human) subjects, each unit containing a predetermined quantity of a presently disclosed agent, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

The dose of a presently disclosed composition, administered to an animal, particularly a human, in the context of the presently disclosed subject matter should be sufficient to produce at least a detectable amount of a diagnostic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, and the like. The size of the dose also will be determined by the existence of any adverse side effects that may accompany the particular agent, or composition thereof, employed. It is generally desirable, whenever possible, to keep adverse side effects to a minimum. The dose of the biologically active material will vary; suitable amounts for each particular agent will be evident to a skilled worker.

A "pharmaceutically acceptable carrier" refers to a biocompatible solution, having due regard to sterility, isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier also can contain stabilizers, preservatives, antioxidants, or other additives, which are well known to one of skill in the art, or other vehicles as known in the art.

iv. General Definitions

Although specific terms are employed herein, they are used in a generic and descriptive sense only and not for purposes of limitation. Particular definitions are provided herein for clarity. Unless otherwise defined, all technical and scientific terms used herein have the same meaning as commonly understood by one of ordinary skill in the art to which this presently described subject matter belongs.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells.

By "control" is meant a standard or reference condition.

By "disease" is meant any condition or disorder that damages or interferes with the normal function of a cell, tissue, organ, organism, or subject.

The term "administering" as used herein refers to contacting a subject with a presently disclosed agent.

By "delivery device" is meant any device that provides for the release of an imaging agent. Exemplary delivery devices include tablets and pills, described below, as well as syringes, osmotic pumps, indwelling catheters, delayed-release and sustained-release biomaterials.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Example 1

Overview

Prostate-specific membrane antigen (PSMA) is overexpressed in the epithelium of prostate cancer and nonprostate solid tumor neovasculature. PSMA is increasingly utilized as a target for cancer imaging and therapy. The synthesis and binding affinities of three low-molecular-weight PSMA-based compounds YC-88, YC-71 and YC-XY-01 are described herein.

In particular, the synthesis and in vivo biodistribution of 2-[3-(1-carboxy-5-{3-[1-(2-[$^{18}$F]fluoroethyl)-1H-1,2,3-triazol-yl]propanamido}pentyl)ureido]-pentanedioic acid ([$^F$] YC-88), containing an [$^{18}$F]fluoroethyl triazole moiety are provided. [$^{18}$F]YC-88 was synthesized from 2-[$^{18}$F]fluoroethyl azide and the corresponding alkyne precursor in two steps using either a one- or two-pot procedure. [$^{18}$F]YC-88 was also synthesized using a custom-made radiofluorination module. Biodistribution and positron emission tomography (PET) imaging were performed in immunocompromised mice using isogenic PSMA$^+$ PC3 PIP and PSMA PC3 flu xenografts. YC-88 exhibited high affinity for PSMA as evidenced by a $K_i$ value of 12.9 nM.

The non-decay corrected radiochemical yields of [$^{18}$F]YC-88 averaged 14±1% (n=5). Specific radioactivities ranged from 320 to 2,460 Ci/mmol (12-91 GBq/μmol) with an average of 940 Ci/mmol (35 GBq/μmol, n=5). In an immunocompromised mouse model, [$^{18}$F]YC-88 clearly delineated PSMA$^+$ PC3 PIP prostate tumor xenografts in imaging with PET. At 1 h post-injection, 47.58±5.19% injected dose per gram of tissue (% ID/g) was evident within the PSMA$^+$ PC3 PIP tumor, with a ratio of 170:1 of uptake within PSMA$^+$ PC3 PIP to PSMA PC3 flu tumor placed in the opposite flank. The tumor-to-kidney ratio at 2 h post-injection was 4:1. At or after 30 min post-injection, minimal nontarget tissue uptake of [$^{18}$F]YC-88 was observed.

Compared to [$^{18}$F]DCFPyL, which is currently in clinical trials, the uptake of [$^{18}$F]YC-88 within the kidney, liver, and spleen was significantly lower at all time-points studied. At 30 min and 1 h post-injection, salivary gland uptake of [$^{18}$F]YC-88 was significantly less than that of [$^{18}$F]DCFPyL. [$^{18}$F]YC-88 is a new PSMA-targeted PET agent synthesized utilizing click chemistry that demonstrates high PSMA$^+$ tumor uptake in a xenograft model. Because of its low uptake in the kidney, rapid clearance from nontarget organs, and relatively simple one-pot, two-step radiosynthesis, [$^{18}$F]YC-88 is a viable new PET radiotracer for imaging PSMA-expressing lesions.

Example 2

Material and Methods

General procedures. All reagents and solvents were American Chemical Society (ACS) or High Performance Liquid Chromatography (HPLC) purity and were purchased from either Sigma-Aldrich (Milwaukee, Wis.) or Fisher Scientific (Pittsburgh, Pa.), except where noted. $^1$H NMR spectra were obtained on a Bruker Avance 400 mHz or 500 MHz Spectrometer. ESI mass spectra were obtained on a Bruker Esquire 3000 plus system. High-resolution mass spectrometry (HR-MS) was done by the Mass Spectrometry Facility at the University of Notre Dame using ESI by direct infusion on a Bruker micrOTOF-II. High performance liquid chromatography (HPLC) purification were performed on a Waters 625 LC system with a Waters 490E multiwavelength UV/V is detector (Milford, Mass.) or on a Varian Prostar System. [$^{18}$F] Fluoride was produced by 18 MeV proton bombardment of a high pressure [$^{18}$O]H$_2$O target using a General Electric PET trace biomedical cyclotron (Milwaukee, Wis.). [$^{18}$F]DCFPyL was prepared as previously published (Szabo et al., *Molecular Imaging and Biology* 2015). Reverse phase radio-HPLC purification was performed using a Varian Prostar System with a Bioscan Flow Count PMT radioactivity detector (Varian Medical Systems, Washington, D.C.). Radioactivity was measured in a Capintec CRC-10R dose calibrator (Ramsey, N.J.). The specific radioactivity was calculated as the radioactivity eluting at the retention time of the product during the semipreparative HPLC purification divided by the mass (determined from a standard curve) corresponding to the area under the curve of the UV absorption.

Synthesis of 2-{3-[1-carboxy-5-(pent-4-ynamido)pentyl]ureido}pentanedioic acid (YC-88)

Di-tert-butyl ((1-(tert-butoxy)-1-oxo-6-(pent-4-ynamido)hexan-2-yl)carbamoyl)glutamate (2). Referring to Scheme 1, to the formate salt of 6-(tert-butoxy)-5-(3-(1,5-di-tert-butoxy-1,5-dioxopentan-2-yl)ureido)-6-oxohexan-1-aminium 1 (0.049 g, 0.09 mmol) (Maresca et al., *J. Med. Chem.* 2009) in CH$_2$Cl$_2$ (2 mL) was added triethylamine (0.04 mL, 0.29 mmol), followed by N-succinimidyl-4-pentynoate (0.030 g, 0.15 mmol). After stirring for 2 h at ambient temperature, the solvent was evaporated. The crude material was purified on a silica gel column using methanol/methylene chloride (5:95) to afford 0.051 g (98%) of compound 2. 1H NMR (400 MHz, CDCl3) δ 6.35 (m, 1H), 5.28-5.37 (m, 2H), 4.25-4.30 (m, 2H), 3.16-3.30 (m, 2H), 2.49-2.52 (m, 2H), 2.38-2.42 (m, 2H), 2.27-2.33 (m, 2H), 1.98-2.10 (m, 2H), 1.80-1.90 (m, 1H), 1.32-1.58 (m, 33H). ESI-Mass calcd for C$_{17}$H$_{25}$FN$_3$O$_8$ [M]+567.3, found 567.9.

2-{3-[1-Carboxy-5-(pent-4-ynamido)pentyl]ureido}-pentanedioic Acid (3). A solution of TFA in CH$_2$Cl$_2$ (1:1, 2 mL) was added to 2 (0.051 g, 0.09 mmol). The mixture was stirred at ambient temperature for 2 h, then concentrated on a rotary evaporator. The crude material was purified by HPLC (Phenomenex C18 10μ, 250×10 mm, H2O/CH3CN/TFA [90/10/0.1], 4 mL/min) to afford 0.028 g (78%) of 3. 1H NMR (400 MHz, D2O/CD3CN=1:1 (v/v)) δ 4.15-4.18 (m, 1H), 4.08-4.11 (m, 1H), 3.07-3.10 (m, 2H), 2.35-2.40 (m, 4H), 2.25-2.32 (m, 3H), 1.99-2.07 (m, 1H), 1.78-1.88 (m, 1H), 1.67-1.75 (m, 1H), 1.53-1.63 (m, 1H), 1.37-1.44 (m, 2H), 1.29-1.34 (m, 2H). ESI-mass calcd for C$_{17}$H$_{25}$FN$_3$O$_8$ [M]+399.2; found, 399.9.

2-[3-(1-Carboxy-5-{3-[1-(2-fluoroethyl)-1H-1,2,3-triazol-yl]propanamido}pentyl)ureido]pentanedioic Acid, YC-88. To a solution of CuSO$_4$ (0.0016 g, 0.01 mmol) and sodium ascorbate (0.004 g, 0.02 mmol) in water (0.1 mL) under nitrogen was added 3 (0.006 g, 0.011 mmol) in 0.05 mL of DMF, followed by a solution of 2-fluoroethyl azide (0.022 mmol) (Glaser and Arstad, *Bioconjugate Chem.* 2007) in DMF (0.5 mL). The reaction mixture was stirred overnight at room temperature. The solvent was evaporated under high vacuum, and the resulting residue was purified by HPLC (Phenomenex C18 10μ, 250×10 mm, H$_2$O/CH$_3$CN/TFA [93/7/0.1], 6 mL/min) to afford 0.004 g (54%) of YC-88. $^1$H NMR (500 MHz, D2O/CD3CN=1:1 (v/v) δ 7.69 (s, 1H), 4.77-4.79 (m, 1H), 4.68-4.69 (m, 1H), 4.62-4.64 (m, 1H), 4.57-4.59 (m, 1H), 4.14-4.17 (m, 1H), 4.08-4.09 (m1H), 3.01-3.03 (m, 2H), 2.89-2.91 (m, 2H), 2.45-2.48 (m, 2H), 2.35-2.38 (m, 2H), 2.01-2.05 (m, 1H), 1.79-1.86 (m, 1H), 1.65-1.72 (m, 1H), 1.51-1.59 (m, 1H), 1.31-1.36 (m, 2H), 1.20-1.25 (m, 2H). HR-MS calcd for C19H30FN6O8+ 489.2109; found, 489.2112 [M+H]$^+$., Scheme 1. Synthesis of radiolabeled compound [$^{18}$F] YC-88 and cold YC-88 (procedures 1 and 2).

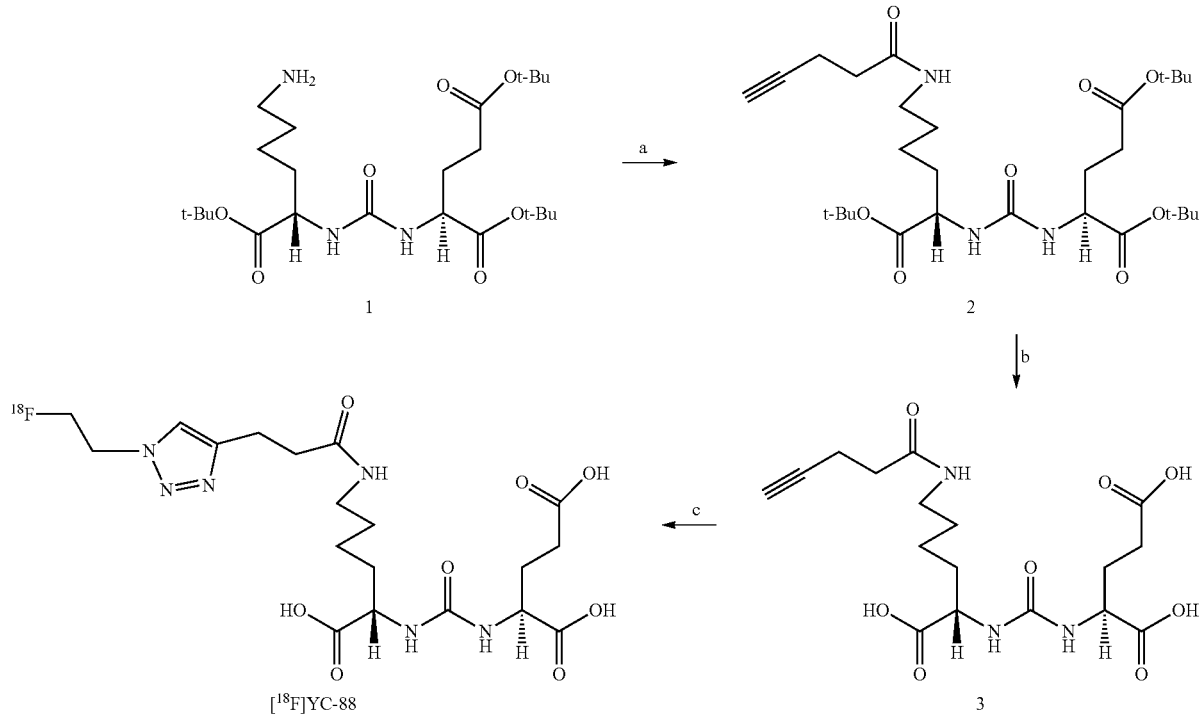

Reagents and conditions:
a Et$_3$N, N-succinimidyl-4-pentynoate, CH$_2$Cl$_2$;
b TFA, CH$_2$Cl$_2$;
c [$^{18/19}$F] 2-fluoroethyl azide, CuSO$_4$, sodium ascorbate, DMF, H$_2$O.

Di-tert-butyl ((1-(tert-butoxy)-1-oxo-6-(3-(1-(2-(tosyloxy)ethyl)-1H-1,2,3-triazol-4-yl)propanamido)hexan-2-yl)carbamoyl)glutamate (3'). Referring now to Scheme 2, to a solution of 2 (0.057 g, 0.01 mmol) in 1 mL DMF under nitrogen was added 2-azidoethyl-4-toluenesulfonate (0.048 g, 0.2 mmol), followed by CuSO$_4$ (0.008 g, 0.05 mmol) and sodium ascorbate (0.020 g, 0.1 mmol) in water (0.2 mL) was added. The reaction mixture was stirred overnight at room temperature. The solvent was evaporated under high vacuum and the resulting residue was purified by Spe-Pak C18 cartridge to afford 0.024 g (30%) of 3'. $^1$H NMR (500 MHz, MeO) δ 7.67 (d, 2H, J=8.2 Hz) 7.66 (s, 1H), 7.42 (d, 2H, J=8.2 Hz) 4.64-4.66 (m, 2H), 4.41-4.43 (m, 2H), 4.20-4.22 (m, 1H), 4.12-4.15 (m, 1H), 3.16-3.19 (m, 2H), 2.95-2.98 (m, 2H), 2.53-2.56 (m, 2H), 2.47 (s, 3H), 2.31-2.36 (m, 2H), 2.03-2.10 (m, 1H), 1.73-1.86 (m, 2H), 1.59-1.65 (m, 1H), 1.46-1.52 (m, 29H), 1.36-1.39 (m, 2H). MS calcd for C$_{38}$H$_{61}$N$_6$O$_{11}$S 809.4, found 809.3 [M+H]$^+$.

Scheme 2. Synthesis of radiolabeled compound [$^{18}$F] YC-88 (procedure 3).

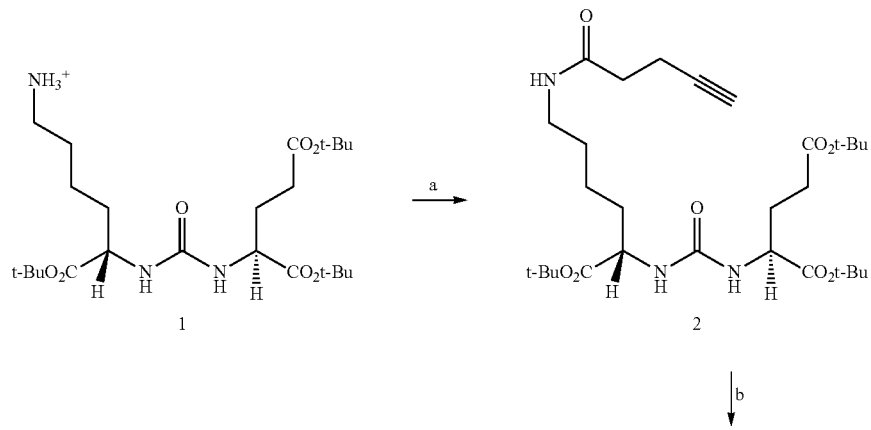

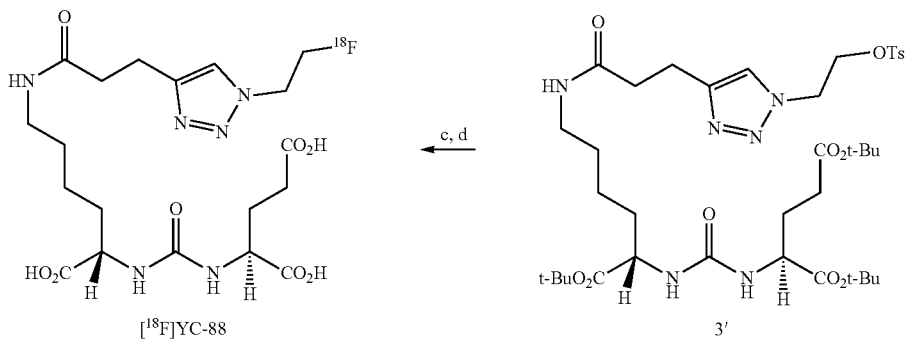

Reagents and conditions:
a Et₃N, N-Succinimidyl 4-pentynoate, CH₂Cl₂;
b 2-azidoethyl-4-toluenesulfonate, CuSO₄, Sodium Ascorbate, DMF and H₂O;
c TBABC, CH₃CN;
d Phosphoric acid.

Synthesis of 30-[1-(2-fluoroethyl-1H-1,2,3-triazol-4-yl]-5,13,20,28-tetraoxo-4,6,12,21,27-pentaazatriacontane-1,3,7,22-tetracarboxylic acid (YC-71)

Referring now to Scheme 3, to a solution of 4 (0.020 g, 0.028 mmol) in DMSO (0.4 mL) was added N,N-diisopropylethylamine (0.025 mL, 0.143 mmol), followed by N-succinimidyl 4-pentynoate (0.007 g, 0.036 mmol). After 2 hours at room temperature, the reaction mixture was purified by a C18 Sep Pak Vac 2 g column using a stepwise gradient of 0-40% aqueous acetonitrile (CH₃CN or MeCN) with 0.1% TFA to afford 0.013 g of 5 (68%). $^1$H NMR (400 MHz, D₂O:CD₃CN=1:1 (v/v)) δ 4.17-4.21 (m, 1H), 4.12-4.15 (m, 1H), 4.06-4.09 (m, 1H), 3.03-3.09 (m, 4H), 2.33-2.40 (m, 4H), 2.26-2.31 (m, 3H), 2.14-2.18 (m, 2H), 2.00-2.10 (m, 3H), 1.57-1.85 (m, 5H), 1.39-1.52 (m, 8H), 1.20-1.32 (m, 8H). ESI-Mass calculated for $C_{31}H_{49}FN_5O_{12}$ [M]⁺ 683.4, found 683.9. To a solution of compound 5 (0.005 g, 0.007 mmol) in 0.1 mL of DMF was add a solution of 2-fluoroethyl azide (0.0013 g, 0.015 mmol) in DMF (0.26 mL), followed by a mixture of CuSO₄ (0.0015 g in 0.1 mL H₂O) and sodium ascorbate (0.005 g in 0.1 mL H₂O) The reaction mixture was stirred for 2 h at room temperature and purified by HPLC (Phenomenex C18 10μ, 250×10 mm, H₂O/CH₃CN/TFA [90/10/0.1], 4 mL/min) to afford 0.004 g (71%) of YC-71. $^1$H NMR (400 MHz, D₂O:CD₃CN=1:1 (v/v)) δ 7.79 (s, 1H), 4.80-4.82 (m, 1H), 4.67-4.71 (m, 2H), 4.60-4.63 (m, 1H), 4.07-4.21 (m, 3H), 3.01-3.07 (m, 4H), 2.90-2.94 (m, 2H), 2.46-2.50 (m, 2H), 2.34-2.38 (m, 2H), 2.14-2.17 (m, 2H), 1.99-2.10 (m, 3H), 1.55-1.88 (m, 5H), 1.21-1.50 (m, 16H). ESI-Mass calculated for $C_{33}H_{53}FN_8O_{12}$ [M]⁺ 772.3, found 772.8.

Scheme 3. Synthesis of radiolabeled compound [¹⁸F]YC-71 and cold YC-71.

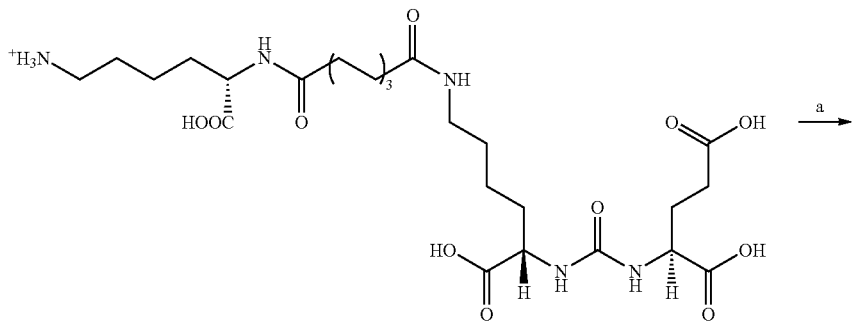

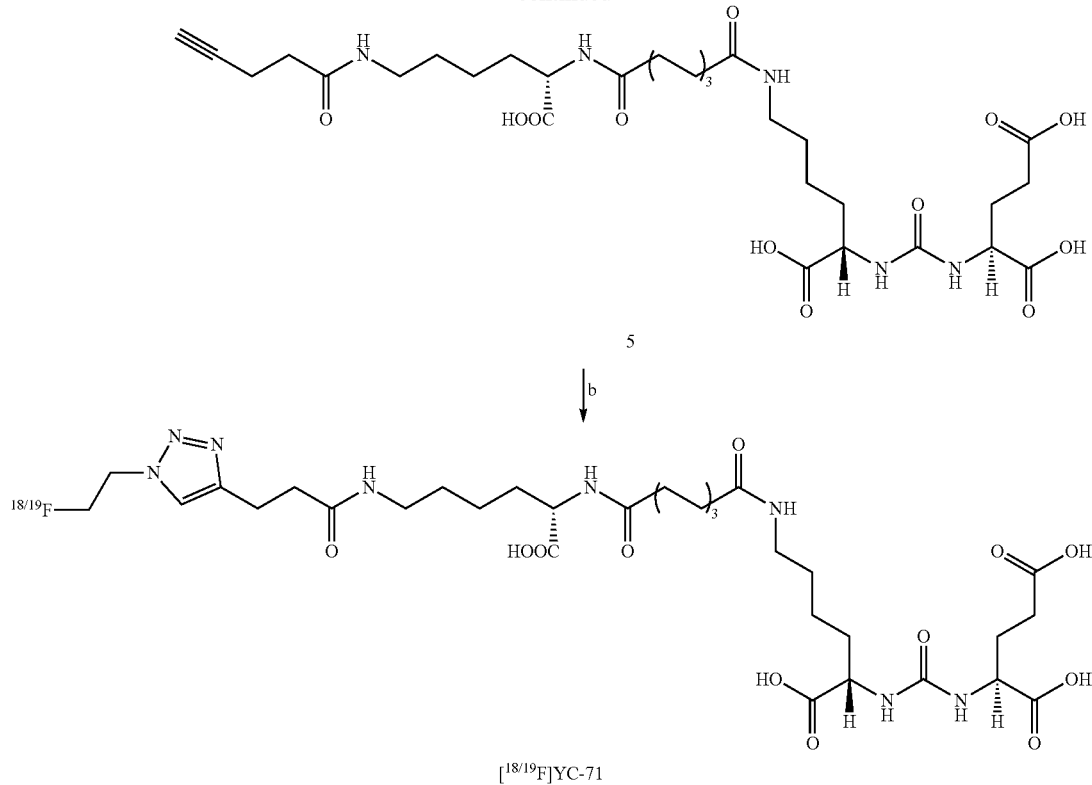

Reagents and conditions:
a DIPEA, N-succinimidyl-4-pentynoate, DMSO;
b [18F]2-fluoroethyl azide, CuSO4, sodium ascorbate, DMF, H2O.

Synthesis of (S)-2-(((((S)-1-carboxy-5-(3-(1-(2-fluoroethyl)-1H-1,2,3-triazol-4-yl) propanamido) pentyl) carbamoyl)oxy)pentanedioic acid (9 or YC-XY-01)

(S) di-tert-butyl 2-((((S)-6-amino-1-(tert-butoxy)-1-oxo-hexan-2-yl)carbamoyl)oxy)pentanedioate (7). (S)-dimethyl 2-hydroxypentanedioate 220 mg (1.25 mmol) and 1,1'-carbonyldiimidazole 300 mg (1.85 mmol) were mixed in 5 mL anhydrous methylene chloride. The reaction was kept at room temperature for 1 h. 290 mg of (S)-dimethyl 2-((1H-imidazole-1-carbonyl)oxy)pentanedioate was obtained by flash column chromatography. The yield is 85%. $^1$H NMR (400 MHz, CDCl$_3$): δ 8.20 (s, 1H), 7.49 (s, 1H), 7.12 (s, 1H), 5.35 (dd, J1=8.0 Hz, J2=4.8 Hz, 1H), 3.83 (s, 3H), 3.72 (s, 3H), 2.58-2.34 (m, 4H). 13C NMR (125 MHz, CDCl$_3$) δ 172.3, 168.7, 148.0, 137.2, 131.0, 117.2, 74.4, 53.0, 29.4, 26.1. MS: 271 (M+H$^+$).

(S)-dimethyl 2-((1H-imidazole-1-carbonyl)oxy)pentanedioate 110 mg (0.41 mmol) was dissolved in MeCN 2 mL and MeI 1 mL. The mixture was sealed and heated at 55 Celsius for 3 hours. The solvent was removed under vacuum. Then, a mixture of Nε-Boc-lysine-tert-butyl ester hydrochloride 275 mg (0.81 mmol) and triethylamine 0.5 mL in 5 mL DMSO was added. The reaction was kept under room temperature overnight. (10S,14S)-10-tert-butyl 14,16-dimethyl 2,2-dimethyl-4,12-dioxo-3,13-dioxa-5,11-diazahexadecane-10,14,16-tricarboxylate was obtained by flash column chromatography in 150 mg. The yield is 75%. $^1$H NMR (400 MHz, CDCl$_3$): δ 5.49 (br, 1H), 5.08-5.06 (m, 1H), 4.70 (br, 1H), 3.80 (s, 3H), 3.73 (s, 3H) 3.16-3.13 (m, 2H), 2.54-2.48 (m, 2H), 2.28-2.17 (m, 2H), 1.89-1.86 (m, 1H), 1.68-1.64 (m, 1H), 1.63-1.41 (m, 22H). $^{13}$C NMR (125 MHz, CDCl$_3$) δ 172.8, 171.3, 170.8, 156.1, 154.9, 82.3, 79.1, 74.6, 71.6, 54.3, 52.4, 51.8, 40.2, 32.5, 29.5, 28.5, 28.0, 26.5, 22.2. MS: 505 (M+H$^+$).

(10S,14S)-10-tert-butyl 14,16-dimethyl 2,2-dimethyl-4,12-dioxo-3,13-dioxa-5,11-diazahexadecane-10,14,16-tricarboxylate 150 mg (0.30 mmol) was treated with a 6 mL solution of TFA/methylene chloride (1/1) for 2 h. The solvent was removed under vacuum and the remaining material was redissolved in 5 mL THF/H$_2$O (1/1). To the solution, LiOH monohydrate 40 mg (1 mmol) was added and the reaction was stirred at room temperature for 4 hours. The final product 7 was purified by HPLC in 80 mg, yield 65%. $^1$H NMR (400 MHz, D$_2$O): δ 4.82-4.77 (m, 1H), 4.11-4.07 (m, 1H), 2.90 (t, J=7.2 Hz, 2H), 2.62-2.42 (m, 2H), 2.14-2.00 (m, 2H), 1.87-1.80 (m, 1H), 1.70-1.60 (m, 3H), 1.41-1.35 (m, 2H). 13C NMR (125 MHz, D$_2$O): δ 177.1, 175.9, 174.6, 157.1, 72.3, 53.7, 39.2, 30.2, 29.3, 26.1, 21.9. MS: 321 (M+H$^+$).

(S)-2-((((S)-1-carboxy-5-(pent-4-ynamido)pentyl)carbamoyl)oxy)pentanedioic acid (8). Referring now to Scheme 4, 23 mg (0.055 mmol) of 7 were dissolved in 1 mL DMSO and 100 μL triethylamine. To the solution, N-succinimidyl 4-pentynoate 15 mg (0.077 mmol) was added. The resulting solution was kept at room temperature for 2 hours. After the solvent removed under vacuum, 18 mg (0.045 mmol) 8 was obtained after HPLC purification. Yield is 81%. MS: 401 (M+H$^+$). HPLC (10-mm×250-mm Phenomenix Luna C18 column, mobile phase 100/0/0.1% to 65/35/0.1% water/acetonitrile/TFA, from 0 minute to 10 minutes, flow 10 mL/min.). 8 eluted at 7.2 minutes.

(S)-2-((((S)-1-carboxy-5-(3-(1-(2-fluoroethyl)-1H-1,2,3-triazol-4-yl)propanamido) pentyl)carbamoyl)oxy)pentanedioic acid (9 or YC-XY-01). 3.5 mg (0.088 mmol) of 8 were dissolved in 2 mL water and the reaction vial was filled with nitrogen. 2-Fluoroethylazide in DMF 1 mL (~2 mg/mL prepared following Bioconjugate Chem. 2007, 18, 989-993) and tetrakis(acetonitrile)copper(I) hexafluorophosphate 2 mg (0.054 mmol) was added. The reaction was kept at room temperature overnight. After the solvent removed under vacuum, 3.3 mg (0.067 mmol) product 9 was obtained after HPLC purification. Yield is 77%. MS: 490 (M+H$^+$). HPLC (10-mm×250-mm Phenomenix Luna C18 column, mobile phase 100/0/0.1% to 65/35/0.1% water/acetonitrile/TFA, from 0 minutes to 15 minutes, flow 8 mL/min.). 9 eluted at 9.5 minutes.

of DMF, 0.1 mL of H2O, CuSO4 (0.1 M, 0.04 mL), and sodium ascorbate (0.2 M, 0.08 mL). The mixture was reacted at ambient temperature for 30 min. The final product [$^{18}$F]YC-88 was obtained after HPLC purification (Phenomenex C18 10 µm, 250×10 mm, H$_2$O/CH$_3$CN/TFA=92/8/0.1, 4 mL/min), and was neutralized with 1 M NaHCO$_3$, concentrated under vacuum to dryness, reconstituted in PBS (pH 7.4), and passed through a 0.22 µm syringe filter into an evacuated sterile vial.

Radiosynthesis of [$^{18}$F]YC-88, Procedure 2 (One-Pot, Two-Step). [$^{18}$F]Fluoride was eluted from a Chromafix 30-PS-HCO$_3$-ion-exchange resin (Macherey-Nagel) with 5 mg of K$_{222}$ and 0.72 mg of KHCO$_3$ in 30% aqueous acetonitrile (1 mL) to a reaction vial and dried by azeotropic distillation at 80° C. with CH$_3$CN (3×0.5 mL) under a stream

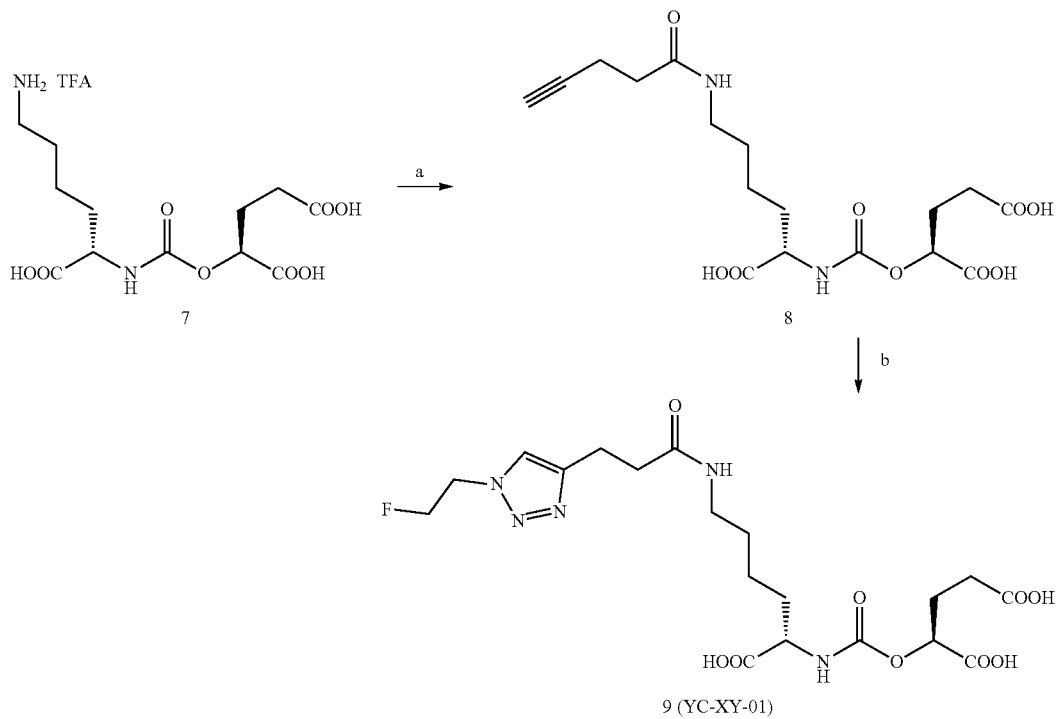

Scheme 4. Synthesis of compound YC-XY-01.

Reagents and conditions:
a Et$_3$N, N-succinimidyl-4-pentynoate, DMSO;
b 2-fluoroethyl azide, tetrakis(acetonitrile) copper (i) hexafluorophosphate, TBTA, H$_2$O/t-BuOH.

Radiosynthesis of [$^{18}$F]YC-88, Procedure 1 (Two-Pot, Two-Step). Referring now to Scheme 1,2-[$^{18}$F]Fluoroethyl azide was synthesized according to a literature procedure (Hugenberg et al., *J. Med. Chem.* 2012). Briefly, [$^{18}$F] fluoride was eluted from a Chromafix 30-PS-HCO$_3$-ion-exchange resin (Macherey-Nagel) with 15 mg of 4,7,13,16,21,24-hexaoxa-1,10-diazabicyclo[8.8.8]hexacosane (K$_{222}$) and 3 mg of K$_2$CO$_3$ in 20% aqueous acetonitrile (1 mL) into a reaction vial and dried by azeotropic distillation at 100° C. with CH$_3$CN (3×0.5) mL under a stream of argon. To the dried [$^{18}$F]KF/K$_{222}$ complex was added 3 µL of 2-azidoethyl 4-toluenesulfonate (Macleod et al., *Synlett* 2010) in 0.3 mL of DMF. The reaction mixture was heated in a sealed vial at 100° C. for 5 min, and then, the 2-[$^{18}$F]fluoroethyl azide was distilled using argon sweep gas into a vial that contained 300 µL of cold DMF. To the vial containing 2-[$^{18}$F]fluoroethyl azide in DMF was added a mixture of 3 (2 mg) in 0.05 mL of argon. To the dried [$^{18}$F]KF/K$_{222}$ complex was added 0.2 mg of 2-azidoethyl 4-toluene sulfonate (Macleod et al., *Synlett* 2010) in 0.2 mL of DMF. The reaction mixture was then heated in a sealed vial at 80° C. for 5 min. CuSO4 (0.2 M, 0.01 mL) and sodium ascorbate (0.4 M, 0.01 mL) were mixed under argon, and to this solution was added 3 (2 mg) in 0.025 mL of DMF. This mixture was then added to the radiofluorination vial containing 2-[$^{18}$F]fluoroethyl azide. This mixture was reacted at 80° C. for 5 min, then cooled to room temperature. The final product [$^{18}$F]YC-88 was obtained by HPLC purification (Phenomenex C18 10 µm, 250×10 mm, H$_2$O/CH$_3$CN/TFA=93/7/0.1, 6 mL/min). The product HPLC fraction was diluted with 30 mL of water and passed through an Oasis HLB cartridge (Waters Corps., Milford, Mass.). The cartridge was washed with 5 mL of water and eluted with 2 mL of ethanol. The ethanol eluent was concentrated under argon, reconstituted in PBS (pH 7.4), and passed through a 0.22 μm syringe filter into an evacuated sterile vial.

Radiosynthesis of [$^{18}$F]YC-88, Procedure 3 (One-Pot, Two-Step with the Radiofluorination Module (RFM)). The custom-made radiofluorination module (RFM) was constructed and controlled in a similar fashion to a previously described microwave radiosynthesis module (Ravert et al., *J. Labelled Compd Rad.* 2014) with the substitution of a thermal heating cavity for the microwave cavity. After all chemicals and components were loaded into the RFM, [$^{18}$F]fluoride ion was delivered to a Chromafix 30-PS-HCO$_3$ SPE cartridge (ABX GmbH, Germany) earlier preconditioned by washing with 1 mL high purity water (Fluka). [$^{18}$O]Water was collected for recycling. Under RFM computer control (National Instruments LabVIEW), the resin cartridge was eluted with a solution of tetrabutylammonium hydrogen carbonate (TBABC) (600 μL, 0.075M, ABX GmbH, Germany) into a 5 mL reaction vial sealed with a multiport cap; the vials were cleaned with dilute nitric acid, washed with HPLC water and dried at 80° C. overnight prior to the synthesis. After rinsing the cartridge with acetonitrile (250 μL, MeCN), the solution was dried at 110° C. with controlled nitrogen flow (325 mL/min) for 150 seconds in a standard thermal heating block. To further dry the [$^{18}$F] fluoride ion, two separate additions of MeCN (250 μL each) were heated for 150 and 180 seconds, respectively.

The vial was cooled using compressed air (flow approx. 6 liters per minute) to a temperature of 50° C. A solution of the YC-88 precursor 3' (5.1 mg, 6.3 μmoles) in MeCN (500 μL) was added to the reaction vial containing the dried [$^{18}$F]fluoride ion. The solution was heated at 50° C. for 12 minutes. This was followed without cooling by the addition of phosphoric acid (85%, 350 μL). The vial was maintained at 45° C. for an additional 6 minutes. A mixture of sodium hydroxide (2 M, 2 mL) and sodium dihydrogen phosphate buffer (10 mM, pH 2.1, 1 mL) was added to quench the reaction and buffer the reaction mixture to a pH of 2-2.5.

The crude reaction mixture was remotely injected onto a Phenomenex Gemini 10×150 mm 5 μm column eluted with a mixture 15/85 Methanol/10 mM phosphate pH 2.2 at flow rate of 10 mL/min. Radiochemical Yield 5%.

Radiosynthesis of [$^{18}$F]YC-71. Referring now to Scheme 3, a mixture of 5 (2 mg) in 0.05 mL DMF, 0.1 mL H$_2$O, CuSO$_4$ (0.1 M, 0.04 mL) and sodium ascorbate (0.2 M, 0.08 mL) was added to the vial containing [$^{18}$F]2-fluoroethyl azide in DMF. The mixture was reacted at room temperature for 30 min. The final product [$^{18}$F]YC-71 was obtained after HPLC purification (Phenomenex C18 10μ, 250×10 mm, CH$_3$CN:H$_2$O:TFA=15/85/0.1, 4 mL/min, retention time: 22 min), and was neutralized with 1M NaHCO$_3$, concentrated under vacuum to dryness, reconstituted in PBS (pH 7.4) and passed through a 0.22-μm syringe filter into an evacuated sterile vial.

Lipophilicity Determination. Octanol-water partition coefficients [log P (pH 7.4) values] were determined according to a literature procedure (Banerjee et al., *J. Med. Chem.* 2010). Briefly, a solution of either [$^{18}$F]YC-88 or [$^{18}$F]DCFPyL was added to a presaturated solution of 1-octanol (5 mL) mixed with phosphate buffered saline (PBS) (5 mL) in a 15 mL centrifuge tube. After vigorously shaking the mixture, it was centrifuged at 3,000 rpm for 5 min. Aliquots were removed from the two phases, and the radioactivity was measured in a 1282 Compugamma CS γ-counter, (LKB, Wallac, Turku, Finland).

NAALADase Assay (Kozikowski et al., *J. Med. Chem.* 2004). The binding affinities of compounds YC-88, YC-71 and YC-XY-01 were tested with an established protocol. Briefly, cell lysates of Lymph Node Carcinoma of the Prostate (LNCaP) cell extracts (25 μL) were incubated with the inhibitor (12.5 μL) in the presence of 4 μM N-acetylaspartylglutamate (NAAG) (12.5 μL) at 37° C. for 120 min. The amount of the glutamate released by NAAG hydrolysis was measured by incubating with a working solution (50 μL) of the Amplex Red Glutamic Acid Kit (Life Technologies, Grand Island, N.Y.) at 37° C. for 60 min. Fluorescence was measured with a VICTOR$^3$V multilabel plate reader (Perkin Elmer Inc., Waltham, Mass.) with excitation at 490 nm and emission at 642 nm. Inhibition curves were determined using semi-log plots and IC$_{50}$ values were determined at the concentration at which enzyme activity was inhibited by 50%. Assays were performed in triplicate with the entire inhibition study being repeated at least once to confirm affinity and mode of inhibition. Enzyme inhibitory constants (K$_i$ values) were generated using the Cheng-Prusoff conversion. Assays were performed in triplicate. Data analysis was performed using GraphPad Prism version 4.00 for Windows (GraphPad Software, San Diego, Calif.).

Cell Lines and Tumor Models. PSMA$^+$ PC3 PIP and PSMA-PC3 flu cell lines were obtained from Dr. Warren Heston (Cleveland Clinic) and were maintained as previously described (Mease et al., *Clin. Cancer Res.* 2008). Cells were grown to 80-90% confluence in a single passage before trypsinization and formulation in Hank's balanced salt solution (HBSS, Sigma, St. Louis, Mo.) for implantation into mice. Animal studies were carried out in compliance with guidelines related to the conduct of animal experiments of the Johns Hopkins Animal Care and Use Committee. For biodistribution and imaging studies, male Nonobese diabetic/severe combined immunodeficiency (NOD-SCID) mice (JHU, in house colony) were implanted subcutaneously with 1×106 PSMA$^+$ PC3 PIP and PSMA$^-$ PC3 flu cells in opposite flanks. Mice were imaged or used in biodistribution studies when the tumor xenografts reached 3-5 mm in diameter.

Biodistribution. PSMA$^+$ PC3 PIP and PSMA$^-$ PC3 flu xenograft-bearing NOD-SCID mice were injected via the tail vein with 0.06 mCi (2.22 MBq) of [$^{18}$F]YC-88 or [$^{18}$F]DCFPyL. In each case, three to four mice per group were sacrificed by cervical dislocation at 30, 60, 120, 240 min post-injection. The heart, lungs, liver, stomach, pancreas, spleen, kidney, fat, muscle, bone, salivary gland, small and large intestines, urinary bladder, PSMA$^+$ PC3 PIP, and PSMA$^-$ PC3 flu tumors were quickly removed. Stomach and GI contents were removed and the urinary bladder emptied. A 0.1 mL sample of blood was also collected. Each organ was weighed, and the tissue radioactivity was measured with an automated γ counter (1282 Compugamma CS, Pharmacia/LKBNuclear, Inc., Gaithersburg, Md.). The % ID/g was calculated by comparison with samples of a standard dilution of the initial dose. All measurements were corrected for decay.

Biodistribution Data Analysis. Microsoft Excel was used for data analysis. Statistical significance was calculated using a two-tailed Student's t test. A P-value <0.05 was considered significant.

PET Imaging. NOD-SCID male mice implanted with PSMA$^+$ PC3 PIP and PSMA$^-$ PC3 flu xenografts were used for imaging. 0.36 mCi (13.3 MBq) of [$^{18}$F]YC-88 was injected intravenously in 0.2 mL of PBS, and 0.2 mCi (7.4 MBq) of [$^{18}$F]YC-71 was injected intravenously in 0.2 mL of PBS. Mice were anesthetized with 3% isoflurane in oxygen for induction and maintained under 1.5% isoflurane in oxygen at a flow rate of 0.8 L/min. The images were acquired using an ARGUS small-animal PET/CT scanner (Sedecal, Madrid, Spain) at 30, 60, and 120 min for [$^{18}$F]YC-88, and 10-20, 40-50 and 60-70 min for [$^{18}$F]YC-71. The dwell time at each bed position was 10 min for a total scan time of 20 min. An energy window of 250-700 keV was used. Images were reconstructed using the FORE/2D-OSEM method (two iterations, 16 subsets) and included correction for radioactive decay, scanner dead time, and scattered radiation.

Radiation Dosimetry. The % ID/g data of kidneys for [$^{18}$F]YC-88 and [$^{18}$F]DCFPyL were fit to a single exponential function of the form $A(t)=A_0 e^{-\lambda t}$, with $A_0$ the time-zero % ID/g and $\lambda$ the biological clearance rate in units of per hour. The simulation analysis and modeling software package SAAM II (The Epsilon Group, Charlottesville, Va.) was used to perform the fits. The biological clearance half-lives and areas under the curve (AUC) obtained are summarized in Table 1.

TABLE 1

Biological Clearance Half-Lives and Areas under the Curve (AUC) in Kidneys for [$^{18}$F]YC-88 and [$^{18}$F] DCFPyL

| Agent | Biological half-life (h) | AUC (% ID/g-h) | AUC ratio (agent/YC-88) |
|---|---|---|---|
| [$^{18}$F]YC-88 | 1.52 | 70.7 | 1 |
| [$^{18}$F] DCFPyL | 1.20 | 340.74 | 4.8 |

Example 3

Results and Discussion

Chemical and Radiochemical Synthesis. The chemical syntheses of YC-88, YC-71 and YC-XY-01 are shown in Schemes 1, 3 and 4, respectively. The radiochemical syntheses of [$^{18}$F]YC-88 are shown in Schemes 1 and 2, and the radiochemical synthesis of [$^{18}$F]YC-71 is shown in Scheme 3.

Referring to Scheme 1, the formate salt of protected lysineglutamate-urea 1 (Maresca et al., *J. Med. Chem.* 2009) was reacted with N-succinimidyl 4-pentynoate (Humenik et al., *ChemBioChem* 2007) to generate the alkyne-containing urea 2. Removal of the t-butyl groups in 2 afforded precursor 3. The copper catalyzed click reaction between 3 and 2-fluoroethyl azide afforded YC-88. Three methods for the preparation of [$^{18}$F]YC-88 were investigated. In procedure 1, a two-pot, two-step approach was used. First, 2-[$^{18}$F]fluoroethyl azide was synthesized from 2-azidoethyl-4-toluenesulfonate and was then purified by distillation (Hugenberg et al., *J. Med. Chem.* 2012) into a chilled receiving vessel. In the second step, precursor 3 and the click reagents copper(II) sulfate and sodium ascorbate were added to the receiving vessel to produce [$^{18}$F]YC-88. Using procedure 1, the non-decay corrected radiochemical yields of two syntheses of [$^{18}$F]YC-88 were 11% and 16%, respectively, based on the starting [$^{18}$F]fluoride. The total synthetic time was approximately 110 min [including drying of [$^{18}$F]fluoride and semipreparative high performance liquid chromatography (HPLC)]. Starting from 40 or 68 mCi (1,480 or 2,516 MBq) of [$^{18}$F]fluoride, the specific radioactivities of [$^{18}$F]YC-88 were 200 and 850 Ci/mmol, respectively (7.4 and 31.5 GBq/µmol). Although procedure 1 was simple, the distillation step made it potentially difficult to incorporate into an automated radiosynthesis module.

In order to modify the radiosynthesis of [$^{18}$F]YC-88 to make it more amenable to automation, a one-pot, two-step method (procedure 2) was investigated. 2-[$^{18}$F]Fluoroethyl azide was synthesized from 2-azidoethyl-4-toluenesulfonate as above, followed by the direct addition of precursor 3, copper(II) sulfate, and sodium ascorbate, to produce [$^{18}$F]YC-88. The non-decay corrected radiochemical yields of [$^{18}$F]YC-88 in the one-pot approach averaged 14±1% based on starting [$^{18}$F]fluoride (n=5). The total synthetic time was approximately 60 min (including drying of [$^{18}$F]fluoride and semipreparative HPLC). Starting from 13-72 mCi (481-2,664 MBq) of [$^{18}$F]fluoride, specific radioactivities ranged from 320 to 2,460 Ci/mmol (12-91 GBq/µmol) with an average of 940 Ci/mmol (35 GBq/µmol, n=5).

In a further effort to potentially prepare [$^{18}$F]YC-88 on a commercial scale, a one-pot method using an automated radiosynthesis module (procedure 3) also was investigated. A solution of precursor 3' was added to the reaction vial containing the dried [18F]fluoride ion further followed by the addition of phosphoric acid, then sodium hydroxide and sodium dihydrogen phosphate buffer, to produce [$^{18}$F]YC-88. The non-decay corrected radiochemical yields of [$^{18}$F]YC-88 in the one-pot approach using an automated radiosynthesis module was about 5% based on starting [$^{18}$F]fluoride (n=1).

Lipophilicity. Octanol-water partition coefficient (log P) values were measured by the shake-flask method using 1-octanol and PBS (pH 7.4). The log P of [$^{18}$F]YC-88 at pH 7.4 was −3.91. Using the same method, the log P of [$^{18}$F]DCFPyL was −3.27.

PSMA Inhibition Assay. The PSMA binding affinity of YC-88 were determined using a modification of the Amplex Red glutamic acid assay (Chen et al., *Biochem. Biophys. Res. Commun.* 2009). The $K_i$ value of YC-88 was 12.9 nM with 95% confidence intervals from 8.7 to 19.1 nM). The $K_i$ values for YC-71 and YC-XY-01 were 0.6 nM and 473 nM respectively. For comparison, the $K_i$ values of DCFBC, DCFBzL, and DCFPyL (FIG. 1) were 0.44 nM, 0.19 nM, and 1.1 nM, respectively (Chen et al., *J. Med. Chem.* 2008; Chen et al., *Clin. Cancer Res.* 2011. In summary, compounds YC-88, YC-71 and YC-XY-01 all express high binding affinity to PSMA.

Biodistribution. Table 2 shows the biodistribution of [$^{18}$F]YC-71 in tumor-bearing mice. [$^{18}$F]YC-71 demonstrated selective PSMA$^+$ PC3 PIP tumor uptake, reaching 38.35±3.06% ID/g at 30 min post-injection, which increased to 41.66±8.16% ID/g at 1 h, then decreased to 39.81±3.65% ID/g at 2 h. PSMA$^-$ PC3 flu tumor uptake was low at all time points. The ratio of uptake within PSMA$^+$ PC3 PIP to PSMA$^-$ PC3 flu tumors ranged from 72:1 at 30 min to 323:1 at 2 h post-injection. The kidney uptake was partially due to the high expression of PSMA within proximal renal tubules (Silver et al., *Clin. Cancer Res.* 1997).

TABLE 2

Biodistribution of [$^{18}$F]YC-71 in Tumor-Bearing Mice[a]

| Organ | 30 min | 60 min | 120 min |
|---|---|---|---|
| blood | 0.84 ± 0.15 | 0.24 ± 0.02 | 0.08 ± 0.01 |
| heart | 0.35 ± 0.07 | 0.17 ± 0.04 | 0.07 ± 0.01 |
| lung | 1.55 ± 0.25 | 0.82 ± 0.16 | 0.31 ± 0.03 |
| liver | 18.89 ± 1.36 | 21.52 ± 3.82 | 19.75 ± 0.93 |
| stomach | 0.52 ± 0.09 | 0.32 ± 0.08 | 0.13 ± 0.06 |
| pancreas | 0.62 ± 0.09 | 0.33 ± 0.09 | 0.17 ± 0.06 |
| spleen | 4.92 ± 0.54 | 3.54 ± 0.89 | 0.91 ± 0.53 |
| fat | 0.42 ± 0.07 | 0.32 ± 0.07 | 0.91 ± 0.53 |

TABLE 2-continued

Biodistribution of [$^{18}$F]YC-71 in Tumor-Bearing Mice$^a$

| Organ | 30 min | 60 min | 120 min |
|---|---|---|---|
| kidney | 70.86 ± 7.48 | 70.63 ± 19.18 | 34.35 ± 6.99 |
| sm. intest | 0.38 ± 0.06 | 0.20 ± 0.09 | 0.21 ± 0.04 |
| lrg. intest | 0.65 ± 0.16 | 0.27 ± 0.03 | 0.12 ± 0.06 |
| muscle | 0.24 ± 0.05 | 0.09 ± 0.00 | 0.04 ± 0.01 |
| bone | 0.33 ± 0.15 | 0.15 ± 0.01 | 0.07 ± 0.02 |
| bladder (empty) | 11.68 ± 3.49 | 1.59 ± 1.09 | 6.34 ± 6.91 |
| PSMA$^+$ PIP | 38.35 ± 3.06 | 41.66 ± 8.16 | 39.81 ± 3.65 |
| PSMA$^-$ flu | 0.53 ± 0.13 | 0.28 ± 0.02 | 0.12 ± 0.03 |
| PIP/flu | 72 | 146 | 323 |

$^a$Values are in % ID/g ± SD;
n = 4 per group;
PIP = PSMA$^+$ PC3; and
flu = PSMA$^-$ PC3 tumors Further, to ensure an accurate comparison, biodistributions for [$^{18}$F]YC-88 and [$^{18}$F]DCFPyL were performed on consecutive days using NOD-SCID mice bearing isogenic PSMA$^+$ PC3 PIP and PSMA$^-$ PC3 flu tumors placed in opposite flanks. Results are shown in Tables 3 and 4.

TABLE 3

Biodistribution of [$^{18}$F]YC-88 in Tumor-Bearing Mice

| Organ | 30 min | 60 min | 120 min | 240 min |
|---|---|---|---|---|
| blood | 1.02 ± 0.43 | 0.29 ± 0.08 | 0.28 ± 0.23 | 0.12 ± 0.04 |
| heart | 0.36 ± 0.18 | 0.18 ± 0.06 | 0.07 ± 0.02 | 0.04 ± 0.01 |
| lung | 1.09 ± 0.31 | 0.49 ± 0.24 | 0.22 ± 0.10 | 0.13 ± 0.02 |
| liver | 1.70 ± 0.21 | 1.73 ± 0.14 | 1.74 ± 0.23 | 1.45 ± 0.14 |
| stomach | 0.41 ± 0.14 | 0.34 ± 0.20 | 0.12 ± 0.07 | 0.06 ± 0.02 |
| pancreas | 0.44 ± 0.13 | 0.16 ± 0.06 | 0.11 ± 0.06 | 0.07 ± 0.02 |
| spleen | 1.67 ± 0.46 | 0.69 ± 0.23 | 0.29 ± 0.16 | 0.15 ± 0.05 |
| fat | 0.33 ± 0.08 | 0.31 ± 0.18 | 0.17 ± 0.10 | 0.10 ± 0.04 |
| kidney | 44.08 ± 12.52 | 20.08 ± 8.09 | 10.20 ± 2.76 | 3.84 ± 0.29 |
| small intestine | 0.37 ± 0.11 | 0.23 ± 0.04 | 0.18 ± 0.07 | 0.14 ± 0.03 |
| large intestine | 0.87 ± 0.85 | 0.27 ± 0.14 | 0.31 ± 0.13 | 0.23 ± 0.09 |
| muscle | 0.22 ± 0.07 | 0.11 ± 0.06 | 0.10 ± 0.03 | 0.06 ± 0.03 |
| bone | 0.40 ± 0.16 | 0.16 ± 0.04 | 0.37 ± 0.36 | 0.11 ± 0.03 |
| salivary gland | 0.85 ± 0.39 | 0.31 ± 0.07 | 0.25 ± 0.07 | 0.14 ± 0.02 |
| bladder (empty) | 17.90 ± 14.18 | 7.78 ± 4.15 | 4.33 ± 2.64 | 1.22 ± 0.89 |
| PSMA$^+$ pip | 40.31 ± 5.13 | 47.58 ± 5.19 | 41.29 ± 4.22 | 25.74 ± 7.33 |
| PSMA$^-$ flu | 0.58 ± 0.23 | 0.28 ± 0.13 | 0.17 ± 0.03 | 0.07 ± 0.01 |
| PIP/flu | 70 | 170 | 243 | 368 |
| PIP/kidney | 0.9 | 2.4 | 4.0 | 6.7 |

$^a$Values are in % ID/g ± SD;
n = 3-4 per group;
PIP = PSMA$^+$ PC3; and
flu = PSMA$^-$ PC3 tumors

TABLE 4

Biodistribution of [$^{18}$F]DCFPyL in Tumor-Bearing Mice

| Organ | 30 min | 60 min | 120 min | 240 min |
|---|---|---|---|---|
| blood | 1.67 ± 0.54 | 0.72 ± 0.22 | 0.23 ± 0.05 | 0.11 ± 0.00 |
| heart | 0.84 ± 0.16 | 0.32 ± 0.09 | 0.12 ± 0.01 | 0.06 ± 0.01 |
| lung | 3.00 ± 0.34 | 1.41 ± 0.25 | 0.41 ± 0.09 | 0.16 ± 0.02 |
| liver | 3.54 ± 0.20 | 3.48 ± 0.21 | 3.08 ± 0.13 | 2.30 ± 0.28 |
| stomach | 0.90 ± 0.14 | 0.50 ± 0.10 | 0.21 ± 0.06 | 0.09 ± 0.03 |
| pancreas | 1.07 ± 0.12 | 0.61 ± 0.21 | 0.23 ± 0.05 | 0.09 ± 0.02 |
| spleen | 10.67 ± 1.68 | 5.61 ± 0.56 | 1.64 ± 0.40 | 0.55 ± 0.11 |
| fat | 1.42 ± 0.51 | 0.84 ± 0.44 | 0.15 ± 0.02 | 0.10 ± 0.05 |
| kidney | 135.28 ± 9.75 | 128.13 ± 15.02 | 61.23 ± 20.36 | 19.36 ± 2.32 |
| small intestine | 0.83 ± 0.03 | 0.56 ± 0.12 | 0.55 ± 0.50 | 0.16 ± 0.04 |
| large intestine | 1.17 ± 0.06 | 0.49 ± 0.05 | 0.52 ± 0.35 | 0.83 ± 1.00 |
| muscle | 0.54 ± 0.05 | 0.36 ± 0.18 | 0.08 ± 0.02 | 0.07 ± 0.04 |
| bone | 1.00 ± 0.51 | 0.35 ± 0.07 | 0.37 ± 0.05 | 0.71 ± 0.40 |
| salivary gland | 2.60 ± 0.60 | 1.57 ± 0.18 | 0.43 ± 0.15 | 0.32 ± 0.22 |

TABLE 4-continued

Biodistribution of [$^{18}$F]DCFPyL in Tumor-Bearing Mice

| Organ | 30 min | 60 min | 120 min | 240 min |
|---|---|---|---|---|
| bladder (empty) | 20.28 ± 12.32 | 11.60 ± 5.41 | 11.40 ± 9.95 | 16.85 ± 10.15 |
| PSMA $^+$ pip | 64.85 ± 19.22 | 84.29 ± 12.29 | 69.55 ± 1.71 | 74.34 ± 7.28 |
| PSMA $^-$ flu | 1.50 ± 0.71 | 0.46 ± 0.06 | 0.21 ± 0.06 | 0.21 ± 0.17 |
| PIP/flu | 42 | 183 | 331 | 354 |
| PIP/kidney | 0.5 | 0.7 | 1.1 | 3.8 |

$^a$Values are in % ID/g ± SD;
n = 3-4 per group;
PIP = PSMA $^+$ PC3; and
flu = PSMA $^-$ PC3 tumors

[$^{18}$F]YC-88 demonstrated selective PSMA$^+$ PC3 PIP tumor uptake, reaching 40.31±5.13% ID/g at 30 min post-injection, which decreased to 25.74±7.33 ID/g at 4 h. PSMA$^-$ PC3 flu tumor uptake was low at all time points. The ratio of uptake within PSMA$^+$ PC3 PIP to PSMA$^-$ PC3 flu tumors ranged from 70:1 at 30 min to 368:1 at 4 h post-injection. The kidney uptake was partially due to the high expression of PSMA within proximal renal tubules (Silver et al., Clin. Cancer Res. 1997). Kidney uptake was highest at 30 min post-injection, followed by rapid clearance. The tumor-to-kidney ratio at 2 h for [$^{18}$F]YC-88 was 4:1. The distribution within other, nontarget tissues was also favorable, with rapid clearance.

Low bone uptake (<1% ID/g at all time points) suggests the absence of metabolic defluorination of [$^{18}$F]YC-88. [18F]DCFPyL demonstrated high and prolonged PSMA+ PC3 PIP tumor uptake, reaching 84.29±12.29% ID/g at 1 h. At the early time points, the highest accumulation of radioactivity was observed in the kidneys. Renal uptake of [$^{18}$F]DCFPyL ranged from 123.69±8.05% ID/g at 30 min to 19.36±2.32% ID/g at 4 h post-injection. The tumor-to-kidney ratio for [18F]DCFPyL was 1.1:1 at 2 h. Compared to [$^{18}$F]DCFPyL, [$^{18}$F]YC-88 demonstrated higher tumor-to-kidney ratios at all time points. [$^{18}$F]YC-88 also showed overall lower uptake in normal organs as well as overall faster clearance than [18F]DCFPyL.

Figure 10A:
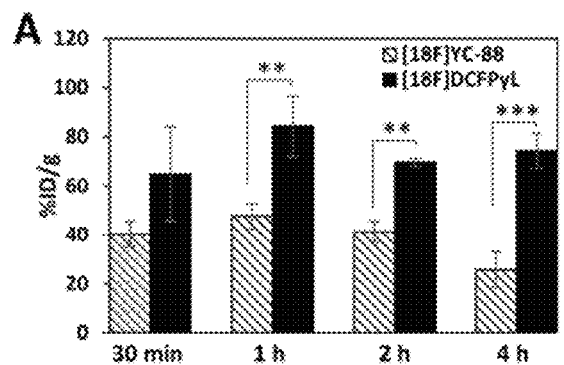
Figure 10B:
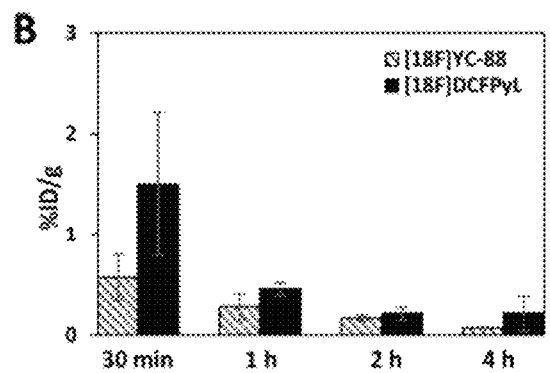
Figure 10C:
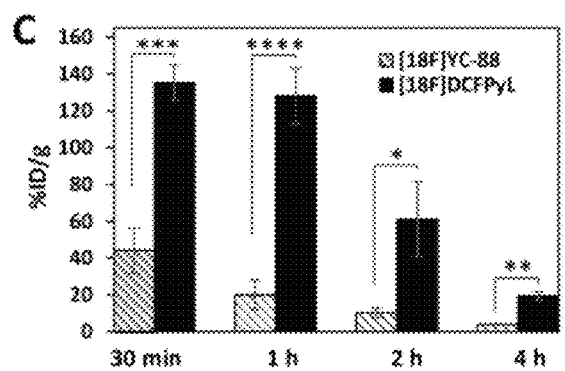
Figure 10D:
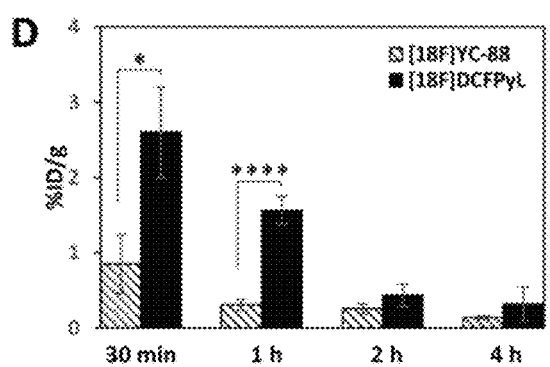
Figure 10E:
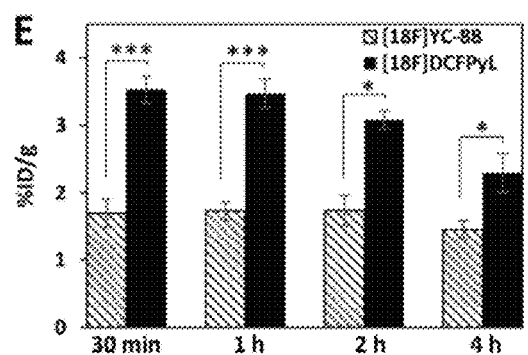
Figure 10F:
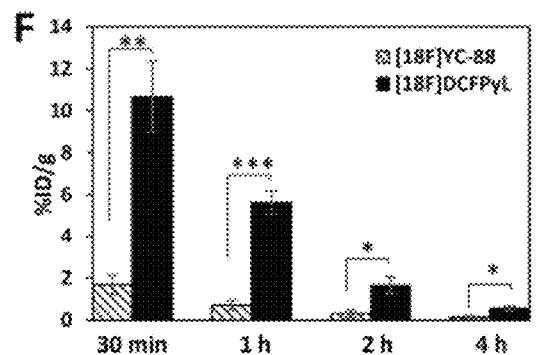

FIG. 10A, FIG. 10B, FIG. 10C, FIG. 10D, FIG. 10E, and FIG. 10F summarize the comparison between selected tissue uptake of [$^{18}$F]YC-88 and [$^{18}$F]DCFPyL. The difference in radiotracer uptake in PSMA$^+$ PC3 PIP tumors (FIG. 10A) was not statistically significant at 30 min (P>0.05), while the PSMA+PC3 PIP tumor uptake of [$^{18}$F]DCFPyL at 1, 2, and 4 h was significantly higher than that of [$^{18}$F]YC-88. There was no significant difference in PSMA$^-$ PC3 flu tumor uptake at any time between the two radiotracers (FIG. 10B). The kidney, liver, and spleen uptake of [$^{18}$F]YC-88 was significantly lower than that for [$^{18}$F]DCFPyL at all time points, as shown in DCFPyL. The kidney absorbed dose with respect to [$^{18}$F]YC-88 showed nearly a 5-fold decrease compared to that of [$^{18}$F]DCFPyL.

Small Animal PET Imaging. Whole body PET images for [$^{18}$F]YC-71 and [$^{18}$F]YC-88 were obtained in male NOD-SCID mice bearing PSMA$^+$ PC3 PIP and PSMA$^-$ PC3 flu xenografts in opposite flanks. FIG. 12 shows the PET images of [$^{18}$F]YC-71 at 10-20 minutes, 40-50 minutes, and 60-70 post-injection. Intense PSMA$^+$ PC3 PIP tumor uptake was seen as early as 30 min post-injection. These data showed binding of [$^{18}$F]YC-71 to the PSMA-expressing PC3-PIP tumor and no significant binding to the PSMA-negative PC3-flu tumor.

FIG. 13 shows the PET images of [$^{18}$F]YC-88 at 30, 60, and 120 min post-injection. Intense PSMA$^+$ PC3 PIP tumor uptake was seen as early as 30 min post-injection. As noted above in the biodistribution studies, renal uptake of [$^{18}$F]YC-88 was prominent, partially due to the route of excretion of this hydrophilic compound as well as to specific uptake from the expression of PSMA in mouse proximal tubules (Silver et al., Clin. Cancer Res. 1997). The images also showed extremely low uptake of this radiotracer in normal tissues. Additionally, higher absolute tumor uptake using [$^{18}$F]YC-71 was obtained, while higher tumor/background ratios were achieved using [$^{18}$F]YC-88.

Three low-molecular-weight PSMA-based compounds YC-88, YC-71 and YC-XY-01 were prepared. In particular, [$^{18}$F]YC-88 was synthesized from 2-[$^{18}$F]fluoroethyl azide and alkyne-bearing urea precursor 3, which allowed rapid and simplified radiolabeling. In particular, the one-pot, two-step radiosynthesis of [$^{18}$F]YC-88 was performed under mild reaction conditions and in radiochemical yields suitable for clinical studies. Furthermore, unlike the radiosyntheses of [$^{18}$F]DCFBz and [$^{18}$F]DCFPyL, no intermediate purification or ester hydrolysis steps were required. Only a single, final semipreparative purification by HPLC was needed. This synthesis of [$^{18}$F]YC-88 is simple and should be able to be readily automated.

Moreover, [$^{18}$F]YC-88 was also synthesized using a custom-made radiofluorination module and urea precursor 3', which allowed automated radiolabeling.

In vivo biodistribution studies of [$^{18}$F]YC-88 and [$^{18}$F]DCFPyL showed that that both compounds had high PSMA$^+$ PC3 PIP tumor uptake. However, the tumor uptake of [$^{18}$F]YC-88 was lower than that for [$^{18}$F]DCFPyL. The lower tumor uptake of [$^{18}$F]YC-88 compared to [$^{18}$F]DCFPyL may be due to its lower binding affinity compared to that of [$^{18}$F]DCFPyL, as a result of the fluoroethyl triazole moiety having a weaker interaction with the hydrophobic subpocket of the S1 binding site compared to that of the fluoro-aryl groups of DCFBC, DCFBzL, and DCFPyL (Barinka et al., J. Med. Chem. 2008). However, [$^{18}$F]YC-88 had lower kidney and nontarget tissue uptake, as well as faster clearance than [$^{18}$F]DCFPyL, which might be due to the higher hydrophilicity of [$^{18}$F]YC-88 (log P=−3.91) than [$^{18}$F]DCFPyL (log P=−3.27). The overall lower nontarget tissue uptake of [$^{18}$F]YC-88 will minimize radiation exposure to healthy tissues, particularly dose-limiting organs such as kidneys and salivary glands. In addition, [$^{18}$F]DCFPyL has recently been utilized for PET imaging of metastatic clear cell renal cell carcinoma (Rowe et al., Ann. Nucl. Med. 2015); however, the slow clearance of [$^{18}$F]DCFPyL from the normal kidney might preclude its use for primary renal lesions. The faster renal clearance of [$^{18}$F]YC-88 may permit such an application.

In summary, [$^{18}$F]YC-88 has been synthesized utilizing copper catalyzed 1,3-dipolar cycloaddition chemistry by a convenient, single pot procedure, and also has been synthesized using a custom-made radiofluorination module. [$^{18}$F] YC-88 has suitable uptake in PSMA+ PC3 PIP xenografts and favorable pharmacokinetics, with lower normal organ uptake than [$^{18}$F]DCFPyL, suggesting it as a promising new PET agent for imaging PSMA-expressing lesions.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Afshar-Oromieh, A., Haberkorn, U., Eder, M., Eisenhut, M., and Zechmann, C. M. (2012) [68Ga] Gallium-labelled PSMA ligand as superiorPET tracer for the diagnosis of prostate cancer: comparison with 18F-FECH. *Eur. J. Nucl. Med. Mol. Imaging* 39, 1085-6.

Afshar-Oromieh, A., Haberkorn, U., Hadaschik, B., Habl, G., Eder, M., Eisenhut, M., Schlemmer, H. P., and Roethke, M. C. (2013) PET/MRI with a68Ga-PSMA ligand for the detection of prostate cancer. *Eur. J. Nucl. Med. Mol. Imaging* 40, 1629-30.

Afshar-Oromieh, A., Haberkorn, U., Schlemmer, H. P., Fenchel, M., Eder, M., Eisenhut, M., Hadaschik, B. A., Kopp-Schneider, A., and Rothke, M. (2014) Comparison of PET/CT and PET/MRI hybrid systems using a 68Ga-labelled PSMA ligand for the diagnosis of recurrent prostate cancer: initial experience. *Eur. J. Nucl. Med. Mol. Imaging* 41, 887-97.

Banerjee, S. R., Pullambhatla, M., Byun, Y., Nimmagadda, S., Green, G., Fox, J. J., Horti, A., Mease, R. C., and Pomper, M. G. (2010) 68Ga-Labeled Inhibitors of Prostate-Specific Membrane Antigen (PSMA) for Imaging Prostate Cancer. *J. Med. Chem.* 53, 5333-5341.

Barinka, C., Byun, Y., Dusich, C. L., Banerjee, S. R., Chen, Y., Castanares, M., Kozikowski, A. P., Mease, R. C., Pomper, M. G., and Lubkowski, J. (2008) Interactions between Human Glutamate Carboxypeptidase II and Urea-Based Inhibitors: Structural Characterization. *J. Med. Chem.* 51, 7737-7743.

Chang, S. S. et al. Five different anti-prostate-specific membrane antigen (PSMA) antibodies confirm PSMA expression in tumor-associated neovasculature. *Cancer Res.* 1999, 59, 3192.

Chen, Y., Dhara, S., Banerjee, S. R., Byun, Y., Pullambhatla, M., Mease, R. C., and Pomper, M. G. (2009) A low molecular weight PSMA-based fluorescent imaging agent for cancer. *Biochem. Biophys. Res. Commun.* 390, 624-629.

Chen, Y., Foss, C. A., Byun, Y., Nimmagadda, S., Pullambhatla, M., Fox, J. J., Castanares, M., Lupold, S. E., Babich, J. W., Mease, R. C., et al. (2008) Radiohalogenated Prostate-Specific Membrane Antigen (PSMA)-BasedUreas as Imaging Agents for Prostate Cancer. *J. Med. Chem.* 51, 7933-7943.

Chen, Y., Pullambhatla, M., Foss, C. A., Byun, Y., Nimmagadda, S., Senthamizhchelvan, S., Sgouros, G., Mease, R. C., and Pomper, M. G. (2011)2-(3-{1-Carboxy-5-[(6-[18F] Fluoro-Pyridine-3-Carbonyl)-Amino]-Pentyl}-Urei do)-Pentanedioic Acid, [18F]DCFPyL, a PSMA-Based PET Imaging Agent for Prostate Cancer. *Clin. Cancer Res.* 17, 7645-7653.

Cheng, Y., and Prusoff, W. H. (1973) Relationship between the inhibition constant (K1) and the concentration of inhibitor which causes 50% inhibition (I50) of an enzymatic reaction. *Biochem. Pharmacol.* 22, 3099-3108.

Cho, S. Y., Gage, K. L., Mease, R. C., Senthamizhchelvan, S., Holt, D. P., Jeffrey-Kwanisai, A., Endres, C. J., Dannals, R. F., Sgouros, G., Lodge, M., et al. (2012) Biodistribution, tumor detection, and radiation dosimetry of 18F-DCFBC, a low-molecular-weight inhibitor of prostate-specific membraneantigen, in patients with metastatic prostate cancer. *J. Nucl. Med.* 53, 1883-91.

Dietlein, M., Kobe, C., Kuhnert, G., Stockter, S., Fischer, T., Schomacker, K., Schmidt, M., Dietlein, F., Zlatopolskiy, B. D., Krapf, P., et al. (2015) Comparison of [18F] DCFPyL and [68Ga]Ga-PSMA HBED-CC for PSMA PET Imaging in Patients with Relapsed Prostate Cancer. *Molecular Imaging and Biology* 17, 575-584.

Eiber, M., Maurer, T., Kubler, H., Gschwend, J. E., Souvatzoglou, M., Ruffani, A., Graner, F.-P., Schwaiger, M., Beer, A. J., Haller, B., et al. (2015) Evaluation of Hybrid 68Ga-PSMA Ligand PET/CT in 248 Patients with Biochemical Recurrence After Radical Prostatectomy. *J. Nucl. Med.* 56, 668-74.

Eiber, M., Nekolla, S. G., Maurer, T., Weirich, G., Wester, H.-J., and Schwaiger, M. (2015) (68)Ga-PSMA PET/MR with multi-modality image analysis for primary prostate cancer. *Abdominal Imaging* 40, 1769-1771.

Glaser, M., and Arstad, E. (2007) "Click labeling" with 2-[$^{18}$F]fluoroethylazide for positron emission tomography. *Bioconjugate Chem.* 18, 989-93.

Glaser, M.; Robins, E. G. *Journal of Labelled Compounds and Radiopharmaceuticals* 2009, 52, 407.

Huang, X., Bennett, M., and Thorpe, P. E. (2004) Anti-tumor effects and lack of side effects in mice of an immunotoxin directed against human and mouse prostate-specific membrane antigen. *Prostate* 61, 1-11.

Huang, X.; Bennett, M.; Thorpe, P. E. *Prostate* 2004, 61, 1.

Hugenberg, V., Breyholz, H. J., Riemann, B., Hermann, S., Schober, O., Schafers, M., Gangadharmath, U., Mocharla, V., Kolb, H., Walsh, J., et al. (2012) A New Class of Highly Potent Matrix Metalloproteinase Inhibitors Based on Triazole-Substituted Hydroxamates: (Radio)Synthesis and in Vitro and First in Vivo Evaluation. *J. Med. Chem.* 55, 4714-4727.

Humenik, M., Huang, Y. W., Wang, Y. R., and Sprinzl, M. (2007) C-terminal incorporation of bio-orthogonal azide groups into a protein and preparation of protein-oligodeoxynucleotide conjugates by Cu(I)-catalyzed cycloaddition. *ChemBioChem* 8, 1103-1106.

Kiess, A. P., Banerjee, S. R., Mease, R. C., Rowe, S. P., Rao, A., Foss, C. A., Chen, Y., Yang, X., Cho, S. Y., Nimmagadda, S., et al. (2015) Prostate-specific membrane antigen as a target for cancer imaging and therapy. *Q. J. Nucl. Med. Mol. Imaging* 59, 241-68.

Kozikowski, A. P., Zhang, J., Nan, F., Petukhov, P. A., Grajkowska, E., Wroblewski, J. T., Yamamoto, T., Bzdega, T., Wroblewska, B., and Neale, J. H. (2004) Synthesis of urea-based inhibitors as active site probes of glutamate carboxypeptidase II: efficacy as analgesic agents. J. Med. Chem. 47, 1729-38.

Liu, H., Moy, P., Kim, S., Xia, Y., Rajasekaran, A., Navarro, V., Knudsen, B., and Bander, N. H. (1997) Monoclonal antibodies to the extracellular domain of prostate-specific membrane antigen also react with tumor vascular endothelium. Cancer research 57, 3629-34.

Macleod, F., Lang, S., and Murphy, J. A. (2010) The 2-(2-Azidoethyl)cycloalkanone Strategy for Bridged Amides and Medium-Sized Cyclic Amine Derivatives in the Aube-Schmidt Reaction. Synlett 2010, 529-534.

Mamat, C., Ramenda, T., and Wuest, F. R. (2009) Recent Applications of Click Chemistry for the Synthesis of Radiotracers for Molecular Imaging. Mini-Rev. Org. Chem. 6, 21-34.

Maresca, K. P., Hillier, S. M., Femia, F. J., Keith, D., Barone, C., Joyal, J. L., Zimmerman, C. N., Kozikowski, A. P., Barrett, J. A., Eckelman, W. C., et al. (2009) A series of halogenated heterodimeric inhibitors of prostate specific membrane antigen (PSMA) as radiolabeled probes for targeting prostate cancer. J Med Chem 52, 347-57.

Mease, R. C., Dusich, C. L., Foss, C. A., Ravert, H. T., Dannals, R. F., Seidel, J., Prideaux, A., Fox, J. J., Sgouros, G., Kozikowski, A. P., et al. (2008) N—[N—[(S)-1,3-Dicarboxypropyl]carbamoyl]-4-[18F]-fluorobenzyl-L-cysteine, [18F]DCFBC: a new imaging probe for prostate cancer. Clin. Cancer Res. 14, 3036-43.

Ravert, H. T., Holt, D. P., and Dannals, R. F. (2014) A microwave radiosynthesis of the 4-[F-18]-fluorobenzyl-triphenylphosphonium ion. J Labelled Compd Rad 57, 695-698.

Rowe, S. P., Gage, K. L., Faraj, S. F., Macura, K. J., Cornish, T. C., Gonzalez-Roibon, N., Guner, G., Munari, E., Partin, A. W., Pavlovich, C. P., et al. (2015) 18F-DCFBC PET/CT for PSMA-Based Detection and Characterization of Primary Prostate Cancer. J. Nucl. Med. 56, 1003-10.

Rowe, S. P., Gorin, M. A., Hammers, H. J., Som Javadi, M., Hawasli, H., Szabo, Z., Cho, S. Y., Pomper, M. G., and Allaf, M. E. (2015) Imaging of metastatic clear cell renal cell carcinoma with PSMA-targeted 18F-DCFPyL PET/CT. Ann. Nucl. Med. 29, 877-882.

Schuelke, N., Varlamova, O. A., Donovan, G. P., Ma, D., Gardner, J. P., Morrissey, D. M., Arrigale, R. R., Zhan, C., Chodera, A. J., Surowitz, K. G., et al. (2003) The homodimer of prostate-specific membrane antigen is a functional target for cancer therapy. Proc. Natl. Acad. Sci. U.S.A. 100, 12590-12595.

Silver, D. A., Pellicer, I., Fair, W. R., Heston, W. D., and Cordon-Cardo, C. (1997) Prostate-specific membrane antigen expression in normal and malignant human tissues. Clin. Cancer Res. 3, 81-5.

Szabo, Z., Mena, E., Rowe, S. P., Plyku, D., Nidal, R., Eisenberger, M. A., Antonarakis, E. S., Fan, H., Dannals, R. F., Chen, Y., et al. (2015) Initial Evaluation of [$^{18}$F] DCFPyL for Prostate-Specific Membrane Antigen (PSMA)-Targeted PET Imaging of Prostate Cancer. Molecular Imaging and Biology 17, 565-574.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound having the following structure:

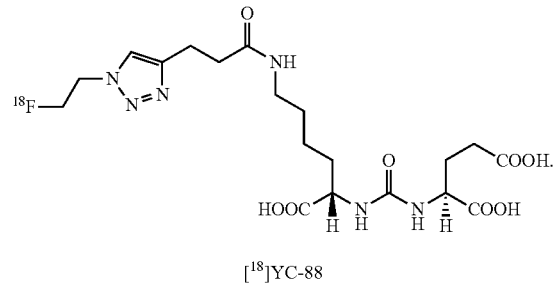 [SMILES: O=C(O)CC[C@H](NC(=O)N[C@@H](CCCCNC(=O)CCc1cn(CC[18F])nn1)C(=O)O)C(=O)O]

[$^{18}$F]YC-88

* * * * *